(12) United States Patent
Arcasoy et al.

(10) Patent No.: US 7,598,057 B2
(45) Date of Patent: Oct. 6, 2009

(54) USE OF CYTOKINE RECEPTORS AS BIOMARKERS AND THERAPEUTIC TARGETS IN HUMAN CANCER

(75) Inventors: Murat O. Arcasoy, Chapel Hill, NC (US); Zishan A. Haroon, Ironwood, MI (US)

(73) Assignee: Duke University, Durham, NC (US)

( * ) Notice: Subject to any disclaimer, the term of this patent is extended or adjusted under 35 U.S.C. 154(b) by 320 days.

(21) Appl. No.: 11/512,501

(22) Filed: Aug. 30, 2006

(65) Prior Publication Data

US 2007/0003969 A1 Jan. 4, 2007

Related U.S. Application Data

(62) Division of application No. 10/625,137, filed on Jul. 23, 2003, now Pat. No. 7,160,697.

(60) Provisional application No. 60/404,870, filed on Aug. 21, 2002.

(51) Int. Cl.
*C12N 15/00* (2006.01)
*C07H 21/04* (2006.01)
*C07K 14/00* (2006.01)

(52) U.S. Cl. .................... 435/69.1; 536/23.1; 536/24.3; 530/350

(58) Field of Classification Search ........................ None
See application file for complete search history.

(56) References Cited

OTHER PUBLICATIONS

Arcasoy et al., Biochem. Biophys. Res. Comm., 2003, vol. 307(4):999-1007.*
Amgen, Inc., "Influence of Erythropoietic Stimulating Agents (ESAS) on Tumor Progression and Survival", 2007 ODAC Meeting Information Package, pp. 127-203.*
International Search Report for PCT/US03/27368, Jun. 29, 2007.
Arcasoy M O, et al. Expression of erythropoietin receptor splice variants in human cancer. Biochemical and Biophysical Research Communications. 2003. vol. 307, pp. 999-1007.
Acs G, et al. Erythropoietin and Erythropoietin Receptor Expression in Human Cancer. Cancer Research. May 1, 2001. vol. 61, pp. 3561-3565.
Mittelman M, et al. Analysis of the erythropoietin receptor gene in patients with myeloproliferative and myelodysplastic syndromes. Leukemia Research. 1996. vol. 20, No. 6, pp. 459-466.
Eck S L and Wilson J M. 1996, in: Goodman and Gilman's The Pharmacological Basis of Therapeutics, Ninth Edition, McGraw-Hill, New York.
Noguchi et al., Cloning of the Human Erythropoietin Receptor Gene, *Blood*, vol. 78, No. 10:2548-2558 (1991).
Nakamura et al., A Truncated Erythropoietin Receptor That Fails to Prevent Programmed Cell Death of Erythoid Cells, *Science*, vol. 257:1138-1141 (Aug. 21, 1992).

\* cited by examiner

*Primary Examiner*—Gary B Nickol
*Assistant Examiner*—Xiaozhen Xie
(74) *Attorney, Agent, or Firm*—Myers Bigel Sibley & Sajovec, P.A.

(57) ABSTRACT

Nucleic acids encoding erythropoietin receptor isoforms are described, as well as the encoded isoforms, methods of detecting the same, and methods of screening for and treating cancer.

8 Claims, 2 Drawing Sheets

Intron 6 insert (Isoform 1)

exon 6 ←┐                    intron 6 insert
... CAC CGC CGg atg gtc agg gaa ggc tcc agg agg agg tga cat cag agt gga aac
    His   Arg   Arg Met Val Arg Glu Gly Ser Arg Arg Arg End ctg aag att gga agg aag cag ccg ctt gaa aag tgg gga gaa gaa aca gca agt gca ┌→ exon 7
    aag gcc ctg agG GCT CT ...

Intron 7 insert (Isoform 2)

exon 7    ←┐  intron 7 insert  ┌→  exon 8
...GGT AAC TTC CAG gtt ggt gct att tct tca gCT GTG GCT GTA CCA GAA TGA ...
   Gly  Asn  Phe  Gln  Val Gly Ala Ile Ser Ser Ala Val  Ala  Val  Pro  Glu  End

Intron 7 unspliced (Isoform 3)

exon 7 ←┐                   intron 7
...TTC CAG gta ggt ggc ctg gtt gtc ccc tca gtg cct ggg ctt ccc tgc ttc ttg cag cca
   Phe   Gln  Val Gly Gly Leu Val Val Pro Ser Val Pro Gly Leu Pro Cys Phe Leu Gln Pro ┌→ exon 8
    aac tgc agg cct ctc tga gca ggt tgg tgc tat ttc ttc agC TGT GGC TGT ...
    Asn Cys Arg Pro Leu End

Intron 5 unspliced (Isoform 4)

exon 5 ←┐                   intron 5
...CCT AGC Ggt gag gcc cca ggc ggg ggt gta gga gga gcc agg gcg aat cac ggg
   Pro   Ser  Gly  Glu Ala Pro Gly Gly Gly Val Gly Gly Ala Arg Ala Asn His Gly ┌→ exon 6
    gca agc cca ccg ccc tga cct cct ccc cgc ctc tta gAC CTG ...
    Ala Ser Pro Pro Pro End

Exon 6 skipped (Isoform 5)

exon 5  ←┬→  exon 7
... ACG CCT AGC GGG CTC TGA AGC AGA ...
   Thr  Pro  Ser  Gly  Leu  End

FIGURE 2

SEQUENCE LISTING

```
<160> NUMBER OF SEQ ID NOS: 21

<210> SEQ ID NO 1
<211> LENGTH: 8647
<212> TYPE: DNA
<213> ORGANISM: Homo sapiens
<220> FEATURE:
<221> NAME/KEY: CDS
<222> LOCATION: (1916)..(2030)
<223> OTHER INFORMATION: exon 1
<220> FEATURE:
<221> NAME/KEY: CDS
<222> LOCATION: (2887)..(3022)
<223> OTHER INFORMATION: exon 2
<220> FEATURE:
<221> NAME/KEY: CDS
<222> LOCATION: (4010)..(4185)
<223> OTHER INFORMATION: exon 3
<220> FEATURE:
<221> NAME/KEY: CDS
<222> LOCATION: (4266)..(4423)
<223> OTHER INFORMATION: exon 4
<220> FEATURE:
<221> NAME/KEY: CDS
<222> LOCATION: (4907)..(5060)
<223> OTHER INFORMATION: exon 5
<220> FEATURE:
<221> NAME/KEY: CDS
<222> LOCATION: (5145)..(5232)
<223> OTHER INFORMATION: exon 6
<220> FEATURE:
<221> NAME/KEY: CDS
<222> LOCATION: (7334)..(7421)
<223> OTHER INFORMATION: exon 7
<220> FEATURE:
<221> NAME/KEY: CDS
<222> LOCATION: (7517)..(8125)
<223> OTHER INFORMATION: exon 8
```

```
<400> SEQUENCE: 1
ggatccaccc acctcggcct cccaaagtgc tgggattaca ggcatgagca ctgtgcatgg      60
actatttatt tattttttg aaacagagtt tcaatcttgt tgcacagcct ggagtgcaat      120
ggtgtgatct cagctcactg caacctctgc cttctggttt caagcaattc tcctgcctca     180
gcctcctgag tagctgggat tacaggcacc caccaccacg ctcgaatata tatatatatt     240
ttttgagacg gagtccgctc tgtcaccagg ctggagtgca gtggcaaat atcggctcac      300 tgaaacctcc ggctcctggg ttcaagcgat tctcctgcag cctcccaagt agctgggatt     360
acaggcatgc agcaccacgc ccatctaatt tttgtatttt tggtagagat ggggttttac     420
catgttggcc aggatggtct tgatctcttg acctcgtgat ctgcccacct cggcctccca     480
aagtgctggg attacaggcg tgacgaccgc gcccggccta cgcctggcta atttttgtat     540
ttttagtaga gacgtggttt cgccatgttg cccaggctgg tctcgaactc ctgacctcat     600
gatccgcctg tctcggcctc ccaaagtgtt gggattacaa gtatgagcca ccgcgccact     660
agccaatttt ttttattttt tgagatgcag tctcactctg ttgcccaggc tggagttgca     720
gtggcatgat cttggctcac tgcaatcttc atctcccaga ctgaagcagt tctcatgcct     780
cagcctcctg agtagctggg attacagcac acgccaccac acctggctaa tttttgtatt     840
tttagtagag atgggatttc accatgttgg ccaggctggt ctcaaactcc tgacctcaag     900
tgatttgccc acgtcggcct cccaaagtgc tgggattata ggcgtgagcc accgccagc      960 ccaagagaat aaaaatgtgg gtggtaaaaa ttttttttccc aaaaattcgt aaatgaaaat   1020
ctcacatatt atgcatactg cccaggagca tggcctagca ctgtgcaaac actcaactgc    1080
tggtcgttgc aaggattatt attggccggc ttcagtggct tgctggtatt cccagcacat    1140
tgggagatgg aggctggagg attgcttaag tccgggattt caagaccagc ctggacaaca    1200
tagtgggatc ccatctctac aaagaatttt aaaaattagc caggtgcagt gggaagattg    1260
cttcagtcca gaggctgcag tgagctatga ttgtgccact gcactccagc ctgggtgaca    1320
gagcaacacc ctgagacaga gagagagagg gggaaggagg gaaggaggga aggaaggaag    1380
gaaggaagga aggaaggaag gaaggaagga aggaaggaaa ggagagagag agagagagag    1440
agagagagag agagagaaaa taatttttat ttatttccag gctggaaga gatgctgatt     1500 tctgcgataa aatcagtagg tacatttttt ggaatgttcg ctatgtgcca ggctagattt    1560
tacagatgag aagtctgaag ctcaggtaag gtaagtcacc tgtccagggc acaaagaaa     1620 aaaaaaacgt gtgtctgaag ccagaacggg agctgttgcg cccaactccc tccctgccc     1680 ccaagcggcc tctgggctcg gaagggccc ctgcctcctc ccgccaggca cttatctcta     1740
cccaggctga gtgctggccc cgcccctcgg ggatctgcca cttagaggcg cctggtcggg    1800
aagggcctgg tcagctgcgt ccggcggagg cagctgctga cccagctgtg gactgtgccg    1860
ggggtggggg acggaggggc aggagccctg ggctccccgt ggcgggggct gtatc atg     1918
                                                                Met
                                                                 1 gac cac ctc ggg gcg tcc ctc tgg ccc cag gtc ggc tcc ctt tgt ctc      1966
Asp His Leu Gly Ala Ser Leu Trp Pro Gln Val Gly Ser Leu Cys Leu
        5                   10                  15 ctg ctc gct ggg gcc gcc tgg gcg ccc ccg cct aac ctc ccg gac ccc      2014
Leu Leu Ala Gly Ala Ala Trp Ala Pro Pro Pro Asn Leu Pro Asp Pro
        20                  25                  30 aag ttc gag agc aaa g gtaaggatga gctgcgtgtg daccccctacg ctggagcctg   2070
Lys Phe Glu Ser Lys
        35
```

-continued

```
caggaccatg ctggggcctg aactcccagc ctaggtcctg ggggccatgc tgtttctgga    2130
cttcctgacc gggtcctggg ggccaagctg gcatctgaac ccttagactg ggtcctggat    2190 gggtggggggg cggggtgggg tatgttagga tccaagactc ctgatcgcgt cccgggcaag   2250
agctagagtg ggcttaacat tcccgtttta ccttttcagg gagtctggga catgctaaat    2310 cctaagggggg ctgacttggt gctaaggtcc ctgggggtg gggaccaagc cgatccctag    2370 gggagggag gtaaagcccg ggtccgagtt agagggccaa gccacaggct actgtaaaca     2430
cggtttgtgt gagggcgcca gatcacttgc ccggcccggt ggaggagggg aggcggggggg   2490 cacggttggc gctatcggtt ggcggggagc ctgccggggc cgatagggggg cccgcctctc   2550 cgcacacacc cccagccgcg cgcgtgtcct aggctggggc ggggctggca gtcccgagct    2610
cgaggtcttg aacgccgcgc ccagctcagc tggccgctgg gtgggcaggt gtgcgccagt    2670
ggtgcacggc gggggacagt aaggcgagaa acttgcccct gggaattagg ggggcaccac    2730
ctctgcggac ccctccaagg gacccgcttg ggaagatggc agggcggggc tttttttctta   2790 tcgggtccgc ccaggctgcg ggagggaaga ggagggggct gtctcccgag gatagagctc    2850
agacccccat gcccttcctt tgtcgcccct ccccag cg gcc ttg ctg gcg gcc       2903
                                          Ala Ala Leu Leu Ala Ala
                                                          40 cgg ggg ccc gaa gag ctt ctg tgc ttc acc gag cgg ttg gag gac ttg      2951
Arg Gly Pro Glu Glu Leu Leu Cys Phe Thr Glu Arg Leu Glu Asp Leu
45               50                  55                  60 gtg tgt ttc tgg gag gaa gcg gcg agc gct ggg gtg ggc ccg ggc aac      2999
Val Cys Phe Trp Glu Glu Ala Ala Ser Ala Gly Val Gly Pro Gly Asn
                 65                  70                  75 tac agc ttc tcc tac cag ctc ga  gtgagtccga tccggcgggt gcctccaagg     3052
Tyr Ser Phe Ser Tyr Gln Leu Glu
             80 gcggagggag ggggtggggc agagctccct ggaggtcgta gcctcgtatg tccccctgctg   3112 tttgaggccc gacggcgcct ccagtcgtgg tcactggagg gaaacctgcg ggtccagggc    3172 tggcacgcct ctatgggccg gggcgcgaac actcccgcga tcaccgctgg aacgcgaccc    3232 caaacatcag gctgggataa caacgcctcc aaatcgaggg taaggcgtta ctacgtcggg    3292 gctgggacgc cttctcgagg tagtatccaa aaggaggcca gcagtgctca tgcctgtaat    3352 cccaactctt tggaaggtcg agcggaagaa ccgcttgagc ccaggtgttc aagaccagcc    3412 tgggcaacac agcgagatcc ccgtctctta aaaaaaaatt agactgggcg cggctgcacg    3472 cctgtaatcc cagcactttg ggaggctgag gcgggcggat cacctgaggt cgggagtttg    3532 agagccagcc tggccaacat ggagaaactc tatctctact aaaaatacaa aattagccgg    3592 gcgtggtggc gcatgcctgt gatcccagct actcgggagg ctgaggcagg agaatcgctt    3652 gaacccggga ggcggaggtt gcggtgagcc gaggtagcgc cattgcactc cagcctgggc    3712 aacaagagcg aaactccgtc tcaaaaaaaa aaaaaataaa agccaggcgt ggcgcgtgcc    3772 tgtggtctca actacttggg aagctgaggt gggaggatcc cttaagcccc agaatttgag    3832 gctgcagtga gccatgatcg cgccactgca ctccagcctg ggcgacgaag gaacaccttg    3892 tcacacacac acacaaggct agaccttgtg tcacacatac acactgcccc ccacaggccg    3952 ggcaatgcca actccccggt ccccccctccc aacctgctcc cttccctggg cgcatag g    4010 gat gag cca tgg aag ctg tgt cgc ctg cac cag gct ccc acg gct cgt      4058
Asp Glu Pro Trp Lys Leu Cys Arg Leu His Gln Ala Pro Thr Ala Arg
85                   90                  95                  100
```

-continued

| | |
|---|---|
| ggt gcg gtg cgc ttc tgg tgt tcg ctg cct aca gcc gac acg tcg agc<br>Gly Ala Val Arg Phe Trp Cys Ser Leu Pro Thr Ala Asp Thr Ser Ser<br>                               105                         110                       115 | 4106 |
| ttc gtc ccc cta gag ttg cgc gtc aca gca gcc tcc ggc gct ccg cga<br>Phe Val Pro Leu Glu Leu Arg Val Thr Ala Ala Ser Gly Ala Pro Arg<br>               120                        125                      130 | 4154 |
| tat cac cgt gtc atc cac atc aat gaa gta g gtaagtgctc tgggaatgga<br>Tyr His Arg Val Ile His Ile Asn Glu Val<br>      135                       140 | 4205 |
| ggagtggtcg gaggagaggg tctcagtcct cgcccacctg accaaccccc atgcctgcag | 4265 |
| tg ctc cta gac gcc ccc gtg ggg ctg gtg gcg cgg ttg gct gac gag<br>   Val Leu Leu Asp Ala Pro Val Gly Leu Val Ala Arg Leu Ala Asp Glu<br>             145                       150                       155 | 4312 |
| agc ggc cac gta gtg ttg cgc tgg ctc ccg ccg cct gag aca ccc atg<br>Ser Gly His Val Val Leu Arg Trp Leu Pro Pro Pro Glu Thr Pro Met<br>               160                        165                      170 | 4360 |
| acg tct cac atc cgc tac gag gtg gac gtc tcg gcc ggc aac ggc gca<br>Thr Ser His Ile Arg Tyr Glu Val Asp Val Ser Ala Gly Asn Gly Ala<br>175                      180                        185                      190 | 4408 |
| ggg agc gta cag agg gtgaggccag cccctacggc ccagccccca aagctccact<br>Gly Ser Val Gln Arg<br>               195 | 4463 |
| gactacggcc cagccacgcc tctcgaggtc gcgcccggtg ccgctttcag ggccggtccg | 4523 |
| taacatccca catcccatta ccctggtgct gaagaccgtt ccacgccac agacacagcc | 4583 |
| cccttttccta atgtcctcgc aagcctgttg aaccccaact tcttctccct ccggccgta | 4643 |
| accctagacc cctttagcgc ccgggtccct ctacgagtgc tagcccagat attaaattgc | 4703 |
| ccgggtcccg ccctttcgta ccagagactc tctctctgat tggccctgag ctttcttggg | 4763 |
| ctcctccccc tactcttatt ggtcccattg caattctagg gcaccgtttt cctttcccct | 4823 |
| gattggctca gttccaccag ggcccgcccc cacgtcatct attttttgtct gctacgcgtc | 4883 |
| cctcgccctg attccgcccc cag gtg gag atc ctg gag ggc cgc acc gag tgt<br>                                          Val Glu Ile Leu Glu Gly Arg Thr Glu Cys<br>                                                                   200                       205 | 4936 |
| gtg ctg agc aac ctg cgg ggc cgg acg cgc tac acc ttc gcc gtc cgc<br>Val Leu Ser Asn Leu Arg Gly Arg Thr Arg Tyr Thr Phe Ala Val Arg<br>             210                        215                        220 | 4984 |
| gcg cgt atg gct gag ccg agc ttc ggc ggc ttc tgg agc gcc tgg tcg<br>Ala Arg Met Ala Glu Pro Ser Phe Gly Gly Phe Trp Ser Ala Trp Ser<br>               225                        230                      235 | 5032 |
| gag cct gtg tcg ctg ctg acg cct agc g gtgaggcccc aggcggggt<br>Glu Pro Val Ser Leu Leu Thr Pro Ser<br>             240                        245 | 5080 |
| gtaggaggag ccagggcgaa tcacggggca agcccaccgc cctgacctcc tccccgcctc | 5140 |
| ttag ac ctg gac ccc ctc atc ctg acg ctc tcc ctc atc ctc gtg gtc<br>       Asp Leu Asp Pro Leu Ile Leu Thr Leu Ser Leu Ile Leu Val Val<br>                    250                        255                     260 | 5188 |
| atc ctg gtg ctg ctg acc gtg ctc gcg ctg ctc tcc cac cgc cg<br>Ile Leu Val Leu Leu Thr Val Leu Ala Leu Leu Ser His Arg Arg<br>          265                        270                       275 | 5232 |
| gtgagctccc catttgggcg ctgggcccag actcctcccc gccaacggtc tctttcact | 5292 |
| atggaaacct aggctcagag agagacacgc acttgcccaa ggtcacgcag taaggattca | 5352 |
| catcagtggc agggctggga tgcatgccag actagaccca gactcttcgt taacattttc | 5412 |
| tgctcttggg gactttcacc tgattttcct tctacatcag gggctgccat ttcttgggtc | 5472 |
| cctttgttag ttcctttccc cagtgtcatc accttttgtaa aatcaactag atggatttag | 5532 |

-continued

```
tgaaagaatt taagaccctg aatgcctccg caccoctgcg gtcaagcttc tcagacacta    5592
tgatcagact agccgttctg aggtatttgt aattccaagc acacactagg tggtttcaca    5652
cccccaagct tttgcccatg ctgttccctc tgcctggaat gcccttcctg ccttgtctgc    5712
taagcaatct tctagtcgtc tttcatggcc ctgttcattt acttggttgg aaaatacaaa    5772
cagagtgcca acatgtgcc aggcactgga gagagaatgg agaacaagct agaccctgac     5832
cacaagtccc tgaccttgtg gatctcaagt caacaaacaa gggacccaag aaatatttga    5892
tgacaaattg taatgagtga tatcacagaa acaaacagaa tgtggtgaca tgacaggatg    5952
gtcagggaag gctccaggag gaggtgacat cagagtggaa acctgaagat tggaaggaag    6012
cagccgcttg aaaagtgggg agaagaaaca gcaagtgcaa aggccctgag gtgggaatga    6072
gattggaacg ttcagccagc ttcaagaatt gccacatgca tggcctggca tggtggctca    6132
cgcctgtaat cccagcactt tgggatgccg aggcaggcag atcacctgag gttgggagtt    6192
cgcgaccagc ctgaccaaca tggagaaacc ccacctctac taaaaataca aaactagcca    6252
agcgtggtgg cacatgcctg taatccccgc tactcgggag gctgaggcag gagaatcact    6312
tgaacctggg aggtggaggt tgcgggtgag ccgagatcgt gccatcgcat tccagcctgg    6372
gcaataagag tgaaactccg tctcaaaaaa aaaaaaaaaa ttgccacatg ctagagtgg    6432 tatgtaaggg ggtgtggcag atattgagat gaggaggtg acaggggtca tataacgcag     6492
ggccttctgc agggtggtgg ggaggagttt ggaatttttt ttttttttga gacagagtca    6552
ctcttgtcgc ccaagctgta gtgcagtgca gcagtcttgg ctcactgcaa ctctgcctcc    6612
caggttcaag tgattctcct gcctcaaccg cctgagtagc tgagattaca ggcgtgcatg    6672
cccggctaat tttgtagttt tagtagagac ggggttccac catgttggcc aggctggtct    6732
caaactcctg acctcaggtg atctgctcac atcagcctct caaagtgctg ggattatagg    6792
catgagccac cgtgcctggc ttggatttta tcctaaatgc ctctctcatt accccagaag    6852
gtaacataat atttatctat gaagtgacat catggacctc ctggaaaaat ctgggccagg    6912
gttttgggtt ttttaattta tttttatttta ttttttttag agatgggggt ctcactatgt    6972
ttcctaggct ggtcttgaac tcctgggttc aaatgatcct cccacctcag cctcccaaag    7032
tactgggatt atagtgctgg tgtaaaccac tgcacctggc catggccagg attaaaggga    7092
gaatgaccaa ggtatattga actcctatgc accccttcaat accctgttcc atttacccctt   7152 ttgtagggcc ttgctgatgc ttcagccaaa acccctgtcc cctggccctg atgtactcct    7212
ctgcctccat tgtgatcaca gggaccaagt gtatctgtgc ctctatgact gggagtggag    7272
ggggaattgg tgagtattca atgagtcata tctatgtaac tatttatatt ggcttcaaca    7332 g g gct ctg aag cag aag atc tgg cct ggc atc ccg agc cca gag agc        7379
    Ala Leu Lys Gln Lys Ile Trp Pro Gly Ile Pro Ser Pro Glu Ser
        280                 285                 290 gag ttt gaa ggc ctc ttc acc acc cac aag ggt aac ttc cag                7421
Glu Phe Glu Gly Leu Phe Thr Thr His Lys Gly Asn Phe Gln
        295                 300                 305 gtaggtggcc tggttgtccc ctcagtgcct gggcttccct gcttcttgca gccaaactgc     7481
aggcctctct gagcaggttg gtgctatttc ttcag ctg tgg ctg tac cag aat         7534
                                  Leu Trp Leu Tyr Gln Asn
                                                310 gat ggc tgc ctg tgg tgg agc ccc tgc acc ccc ttc acg gag gac cca        7582
Asp Gly Cys Leu Trp Trp Ser Pro Cys Thr Pro Phe Thr Glu Asp Pro
        315                 320                 325
```

```
cct gct tcc ctg gaa gtc ctc tca gag cgc tgc tgg ggg acg atg cag       7630
Pro Ala Ser Leu Glu Val Leu Ser Glu Arg Cys Trp Gly Thr Met Gln
        330                 335                 340 gca gtg gag ccg ggg aca gat gat gag ggc ccc ctg ctg gag cca gtg       7678
Ala Val Glu Pro Gly Thr Asp Asp Glu Gly Pro Leu Leu Glu Pro Val
345                 350                 355 ggc agt gag cat gcc cag gat acc tat ctg gtg ctg gac aaa tgg ttg       7726
Gly Ser Glu His Ala Gln Asp Thr Tyr Leu Val Leu Asp Lys Trp Leu
360                 365                 370                 375 ctg ccc cgg aac ccg ccc agt gag gac ctc cca ggg cct ggt ggc agt       7774
Leu Pro Arg Asn Pro Pro Ser Glu Asp Leu Pro Gly Pro Gly Gly Ser
                380                 385                 390 gtg gac ata gtg gcc atg gat gaa ggc tca gaa gca tcc tcc tgc tca       7822
Val Asp Ile Val Ala Met Asp Glu Gly Ser Glu Ala Ser Ser Cys Ser
            395                 400                 405 tct gct ttg gcc tcg aag ccc agc cca gag gga gcc tct gct gcc agc       7870
Ser Ala Leu Ala Ser Lys Pro Ser Pro Glu Gly Ala Ser Ala Ala Ser
        410                 415                 420 ttt gag tac act atc ctg gac ccc agc tcc cag ctc ttg cgt cca tgg       7918
Phe Glu Tyr Thr Ile Leu Asp Pro Ser Ser Gln Leu Leu Arg Pro Trp
425                 430                 435 aca ctg tgc cct gag ctg ccc cct acc cca ccc cac cta aag tac ctg       7966
Thr Leu Cys Pro Glu Leu Pro Pro Thr Pro Pro His Leu Lys Tyr Leu
440                 445                 450                 455 tac ctt gtg gta tct gac tct ggc atc tca act gac tac agc tca ggg       8014
Tyr Leu Val Val Ser Asp Ser Gly Ile Ser Thr Asp Tyr Ser Ser Gly
            460                 465                 470 gac tcc cag gga gcc caa ggg ggc tta tcc gat ggc ccc tac tcc aac       8062
Asp Ser Gln Gly Ala Gln Gly Gly Leu Ser Asp Gly Pro Tyr Ser Asn
        475                 480                 485 cct tat gag aac agc ctt atc cca gcc gct gag cct ctg ccc ccc agc       8110
Pro Tyr Glu Asn Ser Leu Ile Pro Ala Ala Glu Pro Leu Pro Pro Ser
                490                 495                 500 tat gtg gct tgc tct taggacacca ggctgcagat gatcagggat ccaatatgac       8165
Tyr Val Ala Cys Ser
        505 tcagagaacc agtgcagact caagacttat ggaacaggga tggcgaggcc tctctcagga    8225 gcaggggcat tgctgatttt gtctgcccaa tccatcctgc tcaggaaacc acaaccttgc    8285 agtattttta aatatgtata gttttttttt gtatctatat atatatatac acatatgtat    8345 gtaagttttt ctaccatgat ttctacaaac acccttaag tcccatcttc ccctgggcat     8405 aggccatagg gatagaagtt aaagttcttg agcttattca gaagctggat ctgcaatctg    8465 aatgctactc ataacataac aaaatagtat gttaaacagc tcttaaatct tactggctta    8525 ccacattaaa tgatttctct ctcctaactc agctcaaatg ggcagccatc catggatgag    8585 tcagaggttc agactcttcc agtctgtagc tctaccttct cttagggtac ttagatggat    8645 cc                                                                   8647

<210> SEQ ID NO 2
<211> LENGTH: 508
<212> TYPE: PRT
<213> ORGANISM: Homo sapiens

<400> SEQUENCE: 2

Met Asp His Leu Gly Ala Ser Leu Trp Pro Gln Val Gly Ser Leu Cys
1               5                   10                  15

Leu Leu Leu Ala Gly Ala Ala Trp Ala Pro Pro Pro Asn Leu Pro Asp
            20                  25                  30
```

```
Pro Lys Phe Glu Ser Lys Ala Ala Leu Leu Ala Ala Arg Gly Pro Glu
        35                  40                  45

Glu Leu Leu Cys Phe Thr Glu Arg Leu Glu Asp Leu Val Cys Phe Trp
 50                  55                  60

Glu Glu Ala Ala Ser Ala Gly Val Gly Pro Gly Asn Tyr Ser Phe Ser
 65                  70                  75                  80

Tyr Gln Leu Glu Asp Glu Pro Trp Lys Leu Cys Arg Leu His Gln Ala
                 85                  90                  95

Pro Thr Ala Arg Gly Ala Val Arg Phe Trp Cys Ser Leu Pro Thr Ala
                100                 105                 110

Asp Thr Ser Phe Val Pro Leu Glu Leu Arg Val Thr Ala Ala Ser
                115                 120                 125

Gly Ala Pro Arg Tyr His Arg Val Ile His Ile Asn Glu Val Val Leu
        130                 135                 140

Leu Asp Ala Pro Val Gly Leu Val Ala Arg Leu Ala Asp Glu Ser Gly
145                 150                 155                 160

His Val Val Leu Arg Trp Leu Pro Pro Glu Thr Pro Met Thr Ser
                    165                 170                 175

His Ile Arg Tyr Glu Val Asp Val Ser Ala Gly Asn Gly Ala Gly Ser
                180                 185                 190

Val Gln Arg Val Glu Ile Leu Glu Gly Arg Thr Glu Cys Val Leu Ser
            195                 200                 205

Asn Leu Arg Gly Arg Thr Arg Tyr Thr Phe Ala Val Arg Ala Arg Met
    210                 215                 220

Ala Glu Pro Ser Phe Gly Gly Phe Trp Ser Ala Trp Ser Glu Pro Val
225                 230                 235                 240

Ser Leu Leu Thr Pro Ser Asp Leu Asp Pro Leu Ile Leu Thr Leu Ser
                245                 250                 255

Leu Ile Leu Val Val Ile Leu Val Leu Leu Thr Val Leu Ala Leu Leu
            260                 265                 270

Ser His Arg Arg Ala Leu Lys Gln Lys Ile Trp Pro Gly Ile Pro Ser
        275                 280                 285

Pro Glu Ser Glu Phe Glu Gly Leu Phe Thr Thr His Lys Gly Asn Phe
    290                 295                 300

Gln Leu Trp Leu Tyr Gln Asn Asp Gly Cys Leu Trp Trp Ser Pro Cys
305                 310                 315                 320

Thr Pro Phe Thr Glu Asp Pro Pro Ala Ser Leu Glu Val Leu Ser Glu
                325                 330                 335

Arg Cys Trp Gly Thr Met Gln Ala Val Glu Pro Gly Thr Asp Asp Glu
            340                 345                 350

Gly Pro Leu Leu Glu Pro Val Gly Ser Glu His Ala Gln Asp Thr Tyr
        355                 360                 365

Leu Val Leu Asp Lys Trp Leu Leu Pro Arg Asn Pro Pro Ser Glu Asp
    370                 375                 380

Leu Pro Gly Pro Gly Gly Ser Val Asp Ile Val Ala Met Asp Glu Gly
385                 390                 395                 400

Ser Glu Ala Ser Ser Cys Ser Ser Ala Leu Ala Ser Lys Pro Ser Pro
                405                 410                 415

Glu Gly Ala Ser Ala Ala Ser Phe Glu Tyr Thr Ile Leu Asp Pro Ser
            420                 425                 430

Ser Gln Leu Leu Arg Pro Trp Thr Leu Cys Pro Glu Leu Pro Pro Thr
        435                 440                 445
```

```
             Pro Pro His Leu Lys Tyr Leu Tyr Leu Val Val Ser Asp Ser Gly Ile
                 450                 455                 460

Ser Thr Asp Tyr Ser Ser Gly Asp Ser Gln Gly Ala Gln Gly Gly Leu
             465                 470                 475                 480

Ser Asp Gly Pro Tyr Ser Asn Pro Tyr Glu Asn Ser Leu Ile Pro Ala
                             485                 490                 495

Ala Glu Pro Leu Pro Pro Ser Tyr Val Ala Cys Ser
                         500                 505

<210> SEQ ID NO 3
<211> LENGTH: 1865
<212> TYPE: DNA
<213> ORGANISM: Homo sapiens
<220> FEATURE:
<221> NAME/KEY: misc_feature
<222> LOCATION: (1)..(1865)
<223> OTHER INFORMATION: Mature full-length EpoR mRNA
<220> FEATURE:
<221> NAME/KEY: misc_feature
<222> LOCATION: (137)..(1660)
<223> OTHER INFORMATION: Full-length EpoR ORF

<400> SEQUENCE: 3
acttagaggc gcctggtcgg gaagggcctg gtcagctgcg tccggcggag gcagctgctg      60
acccagctgt ggactgtgcc gggggtgggg gacggagggg caggagccct gggctccccg     120 tggcggggc tgtatcatgg accacctcgg ggcgtccctc tggccccagg tcggctccct     180
ttgtctcctg ctcgctgggg ccgcctgggc gccccgcct aacctcccgg accccaagtt     240
cgagagcaaa gcggccttgc tggcggcccg ggggcccgaa gagcttctgt gcttcaccga     300
gcggttggag gacttggtgt gtttctggga ggaagcggcg agcgctgggg tgggcccggg     360
caactacagc ttctcctacc agctcgagga tgagccatgg aagctgtgtc gcctgcacca     420
ggctcccacg gctcgtggtg cggtgcgctt ctggtgttcg ctgcctacag ccgacacgtc     480
gagcttcgtg cccctagagt tgcgcgtcac agcagcctcc ggcgctccgc gatatcaccg     540
tgtcatccac atcaatgaag tagtgctcct agacgccccc gtggggctgg tggcgcggtt     600
ggctgacgag agcggccacg tagtgttgcg ctggctcccg ccgcctgaga cacccatgac     660
gtctcacatc cgctacgagg tggacgtctc ggccggcaac ggcgcaggga gcgtacagag     720
ggtggagatc ctggagggcc gcaccgagtg tgtgctgagc aacctgcggg gccggacgcg     780
ctacaccttc gccgtccgcg cgcgtatggc tgagccgagc ttcggcggct tctggagcgc     840
ctggtcggag cctgtgtcgc tgctgacgcc tagcgacctg accccctca tcctgacgct     900 ctccctcatc ctcgtggtca tcctggtgct gctgaccgtg ctcgcgctgc tctcccaccg     960
ccgggctctg aagcagaaga tctggcctgg catcccgagc ccagagagcg agtttgaagg    1020
cctcttcacc acccacaagg gtaacttcca gctgtggctg taccagaatg atggctgcct    1080
gtggtggagc ccctgcaccc ccttcacgga ggacccacct gcttccctgg aagtcctctc    1140
agagcgctgc tggggacga tgcaggcagt ggagccgggg acagatgatg agggccccct    1200
gctggagcca gtgggcagtg agcatgccca ggatacctat ctggtgctgg acaaatggtt    1260
gctgccccgg aacccgccca gtgaggacct cccagggcct ggtggcagtg tggacatagt    1320
ggccatggat gaaggctcag aagcatcctc ctgctcatct gctttggcct cgaagcccag    1380
cccagaggga gcctctgctg ccagctttga gtacactatc ctgaccccga ctcccagct    1440 cttgcgtcca tggacactgt gccctgagct gccccctacc ccaccccacc taaagtacct    1500
gtaccttgtg gtatctgact ctggcatctc aactgactac agctcagggg actcccaggg    1560
```

-continued

```
agcccaaggg ggcttatccg atggccccta ctccaaccct tatgagaaca gccttatccc    1620
agccgctgag cctctgcccc ccagctatgt ggcttgctct taggacacca ggctgcagat    1680
gatcagggat ccaatatgac tcagagaacc agtgcagact caagacttat ggaacaggga    1740
tggcgaggcc tctctcagga gcaggggcat tgctgatttt gtctgcccaa tccatcctgc    1800
tcaggaaacc acaaccttgc agtattttta aatatgtata gttttttttat atgtatagtt    1860 ttttt                                                                 1865
```

<210> SEQ ID NO 4
<211> LENGTH: 858
<212> TYPE: DNA
<213> ORGANISM: Homo sapiens
<220> FEATURE:
<221> NAME/KEY: CDS
<222> LOCATION: (1)..(855)
<223> OTHER INFORMATION: EpoR Isoform 1, intron 6 insert

<400> SEQUENCE: 4

```
atg gac cac ctc ggg gcg tcc ctc tgg ccc cag gtc ggc tcc ctt tgt      48
Met Asp His Leu Gly Ala Ser Leu Trp Pro Gln Val Gly Ser Leu Cys
1               5                   10                  15 ctc ctg ctc gct ggg gcc gcc tgg gcg ccc ccg cct aac ctc ccg gac      96
Leu Leu Leu Ala Gly Ala Ala Trp Ala Pro Pro Pro Asn Leu Pro Asp
                20                  25                  30 ccc aag ttc gag agc aaa gcg gcc ttg ctg gcg gcc cgg ggg ccc gaa     144
Pro Lys Phe Glu Ser Lys Ala Ala Leu Leu Ala Ala Arg Gly Pro Glu
            35                  40                  45 gag ctt ctg tgc ttc acc gag cgg ttg gag gac ttg gtg tgt ttc tgg     192
Glu Leu Leu Cys Phe Thr Glu Arg Leu Glu Asp Leu Val Cys Phe Trp
        50                  55                  60 gag gaa gcg gcg agc gct ggg gtg ggc ccg ggc aac tac agc ttc tcc     240
Glu Glu Ala Ala Ser Ala Gly Val Gly Pro Gly Asn Tyr Ser Phe Ser
65                  70                  75                  80 tac cag ctc gag gat gag cca tgg aag ctg tgt cgc ctg cac cag gct     288
Tyr Gln Leu Glu Asp Glu Pro Trp Lys Leu Cys Arg Leu His Gln Ala
                85                  90                  95 ccc acg gct cgt ggt gcg gtg cgc ttc tgg tgt tcg ctg cct aca gcc     336
Pro Thr Ala Arg Gly Ala Val Arg Phe Trp Cys Ser Leu Pro Thr Ala
            100                 105                 110 gac acg tcg agc ttc gtg ccc cta gag ttg cgc gtc aca gca gcc tcc     384
Asp Thr Ser Ser Phe Val Pro Leu Glu Leu Arg Val Thr Ala Ala Ser
        115                 120                 125 ggc gct ccg cga tat cac cgt gtc atc cac atc aat gaa gta gtg ctc     432
Gly Ala Pro Arg Tyr His Arg Val Ile His Ile Asn Glu Val Val Leu
    130                 135                 140 cta gac gcc ccc gtg ggg ctg gtg gcg cgg ttg gct gac gag agc ggc     480
Leu Asp Ala Pro Val Gly Leu Val Ala Arg Leu Ala Asp Glu Ser Gly
145                 150                 155                 160 cac gta gtg ttg cgc tgg ctc ccg ccg cct gag aca ccc atg acg tct     528
His Val Val Leu Arg Trp Leu Pro Pro Pro Glu Thr Pro Met Thr Ser
                165                 170                 175 cac atc cgc tac gag gtg gac gtc tcg gcc ggc aac ggc gca ggg agc     576
His Ile Arg Tyr Glu Val Asp Val Ser Ala Gly Asn Gly Ala Gly Ser
            180                 185                 190 gta cag agg gtg gag atc ctg gag ggc cgc acc gag tgt gtg ctg agc     624
Val Gln Arg Val Glu Ile Leu Glu Gly Arg Thr Glu Cys Val Leu Ser
        195                 200                 205 aac ctg cgg ggc cgg acg cgc tac acc ttc gcc gtc cgc gcg cgt atg     672
Asn Leu Arg Gly Arg Thr Arg Tyr Thr Phe Ala Val Arg Ala Arg Met
    210                 215                 220
```

```
gct gag ccg agc ttc ggc ggc ttc tgg agc gcc tgg tcg gag cct gtg        720
Ala Glu Pro Ser Phe Gly Gly Phe Trp Ser Ala Trp Ser Glu Pro Val
225                 230                 235                 240 tcg ctg ctg acg cct agc gac ctg gac ccc ctc atc ctg acg ctc tcc        768
Ser Leu Leu Thr Pro Ser Asp Leu Asp Pro Leu Ile Leu Thr Leu Ser
                245                 250                 255 ctc atc ctc gtg gtc atc ctg gtg ctg ctg acc gtg ctc gcg ctg ctc        816
Leu Ile Leu Val Val Ile Leu Val Leu Leu Thr Val Leu Ala Leu Leu
        260                 265                 270 tcc cac cgc cgg atg gtc agg gaa ggc tcc agg agg agg tga               858
Ser His Arg Arg Met Val Arg Glu Gly Ser Arg Arg Arg
            275                 280                 285
```

<210> SEQ ID NO 5
<211> LENGTH: 285
<212> TYPE: PRT
<213> ORGANISM: Homo sapiens

<400> SEQUENCE: 5

```
Met Asp His Leu Gly Ala Ser Leu Trp Pro Gln Val Gly Ser Leu Cys
1               5                   10                  15

Leu Leu Leu Ala Gly Ala Ala Trp Ala Pro Pro Asn Leu Pro Asp
            20                  25                  30

Pro Lys Phe Glu Ser Lys Ala Ala Leu Leu Ala Ala Arg Gly Pro Glu
        35                  40                  45

Glu Leu Leu Cys Phe Thr Glu Arg Leu Glu Asp Leu Val Cys Phe Trp
    50                  55                  60

Glu Glu Ala Ala Ser Ala Gly Val Gly Pro Gly Asn Tyr Ser Phe Ser
65                  70                  75                  80

Tyr Gln Leu Glu Asp Glu Pro Trp Lys Leu Cys Arg Leu His Gln Ala
                85                  90                  95

Pro Thr Ala Arg Gly Ala Val Arg Phe Trp Cys Ser Leu Pro Thr Ala
            100                 105                 110

Asp Thr Ser Ser Phe Val Pro Leu Glu Leu Arg Val Thr Ala Ala Ser
        115                 120                 125

Gly Ala Pro Arg Tyr His Arg Val Ile His Ile Asn Glu Val Val Leu
    130                 135                 140

Leu Asp Ala Pro Val Gly Leu Val Ala Arg Leu Ala Asp Glu Ser Gly
145                 150                 155                 160

His Val Val Leu Arg Trp Leu Pro Pro Pro Glu Thr Pro Met Thr Ser
                165                 170                 175

His Ile Arg Tyr Glu Val Asp Val Ser Ala Gly Asn Gly Ala Gly Ser
            180                 185                 190

Val Gln Arg Val Glu Ile Leu Glu Gly Arg Thr Glu Cys Val Leu Ser
        195                 200                 205

Asn Leu Arg Gly Arg Thr Arg Tyr Thr Phe Ala Val Arg Ala Arg Met
    210                 215                 220

Ala Glu Pro Ser Phe Gly Gly Phe Trp Ser Ala Trp Ser Glu Pro Val
225                 230                 235                 240

Ser Leu Leu Thr Pro Ser Asp Leu Asp Pro Leu Ile Leu Thr Leu Ser
                245                 250                 255

Leu Ile Leu Val Val Ile Leu Val Leu Leu Thr Val Leu Ala Leu Leu
            260                 265                 270

Ser His Arg Arg Met Val Arg Glu Gly Ser Arg Arg Arg
        275                 280                 285
```

<210> SEQ ID NO 6
<211> LENGTH: 954
<212> TYPE: DNA
<213> ORGANISM: Homo sapiens
<220> FEATURE:
<221> NAME/KEY: CDS
<222> LOCATION: (1)..(951)
<223> OTHER INFORMATION: EpoR Isoform 2, intron 7 insert

<400> SEQUENCE: 6

| | | | | | | | | | | | | | | | | |
|---|---|---|---|---|---|---|---|---|---|---|---|---|---|---|---|---|
| atg | gac | cac | ctc | ggg | gcg | tcc | ctc | tgg | ccc | cag | gtc | ggc | tcc | ctt | tgt | 48 |
| Met | Asp | His | Leu | Gly | Ala | Ser | Leu | Trp | Pro | Gln | Val | Gly | Ser | Leu | Cys | |
| 1 | | | | 5 | | | | | 10 | | | | | 15 | | |
| ctc | ctg | ctc | gct | ggg | gcc | gcc | tgg | gcg | ccc | ccg | cct | aac | ctc | ccg | gac | 96 |
| Leu | Leu | Leu | Ala | Gly | Ala | Ala | Trp | Ala | Pro | Pro | Pro | Asn | Leu | Pro | Asp | |
| | | | 20 | | | | | 25 | | | | | 30 | | | |
| ccc | aag | ttc | gag | agc | aaa | gcg | gcc | ttg | ctg | gcg | gcc | cgg | ggg | ccc | gaa | 144 |
| Pro | Lys | Phe | Glu | Ser | Lys | Ala | Ala | Leu | Leu | Ala | Ala | Arg | Gly | Pro | Glu | |
| | 35 | | | | | 40 | | | | | 45 | | | | | |
| gag | ctt | ctg | tgc | ttc | acc | gag | cgg | ttg | gag | gac | ttg | gtg | tgt | ttc | tgg | 192 |
| Glu | Leu | Leu | Cys | Phe | Thr | Glu | Arg | Leu | Glu | Asp | Leu | Val | Cys | Phe | Trp | |
| 50 | | | | | 55 | | | | | 60 | | | | | | |
| gag | gaa | gcg | gcg | agc | gct | ggg | gtg | ggc | ccg | ggc | aac | tac | agc | ttc | tcc | 240 |
| Glu | Glu | Ala | Ala | Ser | Ala | Gly | Val | Gly | Pro | Gly | Asn | Tyr | Ser | Phe | Ser | |
| 65 | | | | | 70 | | | | | 75 | | | | | 80 | |
| tac | cag | ctc | gag | gat | gag | cca | tgg | aag | ctg | tgt | cgc | ctg | cac | cag | gct | 288 |
| Tyr | Gln | Leu | Glu | Asp | Glu | Pro | Trp | Lys | Leu | Cys | Arg | Leu | His | Gln | Ala | |
| | | | | 85 | | | | | 90 | | | | | 95 | | |
| ccc | acg | gct | cgt | ggt | gcg | gtg | cgc | ttc | tgg | tgt | tcg | ctg | cct | aca | gcc | 336 |
| Pro | Thr | Ala | Arg | Gly | Ala | Val | Arg | Phe | Trp | Cys | Ser | Leu | Pro | Thr | Ala | |
| | | | 100 | | | | | 105 | | | | | 110 | | | |
| gac | acg | tcg | agc | ttc | gtg | ccc | cta | gag | ttg | cgc | gtc | aca | gca | gcc | tcc | 384 |
| Asp | Thr | Ser | Ser | Phe | Val | Pro | Leu | Glu | Leu | Arg | Val | Thr | Ala | Ala | Ser | |
| | 115 | | | | | 120 | | | | | 125 | | | | | |
| ggc | gct | ccg | cga | tat | cac | cgt | gtc | atc | cac | atc | aat | gaa | gta | gtg | ctc | 432 |
| Gly | Ala | Pro | Arg | Tyr | His | Arg | Val | Ile | His | Ile | Asn | Glu | Val | Val | Leu | |
| 130 | | | | | 135 | | | | | 140 | | | | | | |
| cta | gac | gcc | ccc | gtg | ggg | ctg | gtg | gcg | cgg | ttg | gct | gac | gag | agc | ggc | 480 |
| Leu | Asp | Ala | Pro | Val | Gly | Leu | Val | Ala | Arg | Leu | Ala | Asp | Glu | Ser | Gly | |
| 145 | | | | | 150 | | | | | 155 | | | | | 160 | |
| cac | gta | gtg | ttg | cgc | tgg | ctc | ccg | ccg | cct | gag | aca | ccc | atg | acg | tct | 528 |
| His | Val | Val | Leu | Arg | Trp | Leu | Pro | Pro | Pro | Glu | Thr | Pro | Met | Thr | Ser | |
| | | | | 165 | | | | | 170 | | | | | 175 | | |
| cac | atc | cgc | tac | gag | gtg | gac | gtc | tcg | gcc | ggc | aac | ggc | gca | ggg | agc | 576 |
| His | Ile | Arg | Tyr | Glu | Val | Asp | Val | Ser | Ala | Gly | Asn | Gly | Ala | Gly | Ser | |
| | | | 180 | | | | | 185 | | | | | 190 | | | |
| gta | cag | agg | gtg | gag | atc | ctg | gag | ggc | cgc | acc | gag | tgt | gtg | ctg | agc | 624 |
| Val | Gln | Arg | Val | Glu | Ile | Leu | Glu | Gly | Arg | Thr | Glu | Cys | Val | Leu | Ser | |
| | 195 | | | | | 200 | | | | | 205 | | | | | |
| aac | ctg | cgg | ggc | cgg | acg | cgc | tac | acc | ttc | gcc | gtc | cgc | gcg | cgt | atg | 672 |
| Asn | Leu | Arg | Gly | Arg | Thr | Arg | Tyr | Thr | Phe | Ala | Val | Arg | Ala | Arg | Met | |
| 210 | | | | | 215 | | | | | 220 | | | | | | |
| gct | gag | ccg | agc | ttc | ggc | ggc | ttc | tgg | agc | gcc | tgg | tcg | gag | cct | gtg | 720 |
| Ala | Glu | Pro | Ser | Phe | Gly | Gly | Phe | Trp | Ser | Ala | Trp | Ser | Glu | Pro | Val | |
| 225 | | | | | 230 | | | | | 235 | | | | | 240 | |
| tcg | ctg | ctg | acg | cct | agc | gac | ctg | gac | ccc | ctc | atc | ctg | acg | ctc | tcc | 768 |
| Ser | Leu | Leu | Thr | Pro | Ser | Asp | Leu | Asp | Pro | Leu | Ile | Leu | Thr | Leu | Ser | |
| | | | | 245 | | | | | 250 | | | | | 255 | | |
| ctc | atc | ctc | gtg | gtc | atc | ctg | gtg | ctg | ctg | acc | gtg | ctc | gcg | ctg | ctc | 816 |
| Leu | Ile | Leu | Val | Val | Ile | Leu | Val | Leu | Leu | Thr | Val | Leu | Ala | Leu | Leu | |
| | | | 260 | | | | | 265 | | | | | 270 | | | |

-continued

```
tcc cac cgc cgg gct ctg aag cag aag atc tgg cct ggc atc ccg agc      864
Ser His Arg Arg Ala Leu Lys Gln Lys Ile Trp Pro Gly Ile Pro Ser
    275                 280                 285 cca gag agc gag ttt gaa ggc ctc ttc acc acc cac aag ggt aac ttc      912
Pro Glu Ser Glu Phe Glu Gly Leu Phe Thr Thr His Lys Gly Asn Phe
290                 295                 300 cag gtt ggt gct att tct tca gct gtg gct gta cca gaa tga              954
Gln Val Gly Ala Ile Ser Ser Ala Val Ala Val Pro Glu
305                 310                 315
```

<210> SEQ ID NO 7
<211> LENGTH: 317
<212> TYPE: PRT
<213> ORGANISM: Homo sapiens

<400> SEQUENCE: 7

```
Met Asp His Leu Gly Ala Ser Leu Trp Pro Gln Val Gly Ser Leu Cys
1               5                   10                  15

Leu Leu Leu Ala Gly Ala Ala Trp Ala Pro Pro Asn Leu Pro Asp
                20                  25                  30

Pro Lys Phe Glu Ser Lys Ala Ala Leu Leu Ala Ala Arg Gly Pro Glu
            35                  40                  45

Glu Leu Leu Cys Phe Thr Glu Arg Leu Glu Asp Leu Val Cys Phe Trp
        50                  55                  60

Glu Glu Ala Ala Ser Ala Gly Val Gly Pro Gly Asn Tyr Ser Phe Ser
65                  70                  75                  80

Tyr Gln Leu Glu Asp Glu Pro Trp Lys Leu Cys Arg Leu His Gln Ala
                85                  90                  95

Pro Thr Ala Arg Gly Ala Val Arg Phe Trp Cys Ser Leu Pro Thr Ala
            100                 105                 110

Asp Thr Ser Ser Phe Val Pro Leu Glu Leu Arg Val Thr Ala Ala Ser
        115                 120                 125

Gly Ala Pro Arg Tyr His Arg Val Ile His Ile Asn Glu Val Val Leu
    130                 135                 140

Leu Asp Ala Pro Val Gly Leu Val Ala Arg Leu Ala Asp Glu Ser Gly
145                 150                 155                 160

His Val Val Leu Arg Trp Leu Pro Pro Glu Thr Pro Met Thr Ser
                165                 170                 175

His Ile Arg Tyr Glu Val Asp Val Ser Ala Gly Asn Gly Ala Gly Ser
            180                 185                 190

Val Gln Arg Val Glu Ile Leu Glu Gly Arg Thr Glu Cys Val Leu Ser
        195                 200                 205

Asn Leu Arg Gly Arg Thr Arg Tyr Thr Phe Ala Val Arg Ala Arg Met
    210                 215                 220

Ala Glu Pro Ser Phe Gly Gly Phe Trp Ser Ala Trp Ser Glu Pro Val
225                 230                 235                 240

Ser Leu Leu Thr Pro Ser Asp Leu Asp Pro Leu Ile Leu Thr Leu Ser
                245                 250                 255

Leu Ile Leu Val Val Ile Leu Val Leu Leu Thr Val Leu Ala Leu Leu
            260                 265                 270

Ser His Arg Arg Ala Leu Lys Gln Lys Ile Trp Pro Gly Ile Pro Ser
        275                 280                 285

Pro Glu Ser Glu Phe Glu Gly Leu Phe Thr Thr His Lys Gly Asn Phe
    290                 295                 300

Gln Val Gly Ala Ile Ser Ser Ala Val Ala Val Pro Glu
305                 310                 315
```

<210> SEQ ID NO 8
<211> LENGTH: 987
<212> TYPE: DNA
<213> ORGANISM: Homo sapiens
<220> FEATURE:
<221> NAME/KEY: CDS
<222> LOCATION: (1)..(984)
<223> OTHER INFORMATION: EpoR Isoform 3, intron 7 unspliced

<400> SEQUENCE: 8

```
atg gac cac ctc ggg gcg tcc ctc tgg ccc cag gtc ggc tcc ctt tgt      48
Met Asp His Leu Gly Ala Ser Leu Trp Pro Gln Val Gly Ser Leu Cys
1               5                   10                  15 ctc ctg ctc gct ggg gcc gcc tgg gcg ccc ccg cct aac ctc ccg gac      96
Leu Leu Leu Ala Gly Ala Ala Trp Ala Pro Pro Pro Asn Leu Pro Asp
                20                  25                  30 ccc aag ttc gag agc aaa gcg gcc ttg ctg gcg gcc cgg ggg ccc gaa     144
Pro Lys Phe Glu Ser Lys Ala Ala Leu Leu Ala Ala Arg Gly Pro Glu
            35                  40                  45 gag ctt ctg tgc ttc acc gag cgg ttg gag gac ttg gtg tgt ttc tgg     192
Glu Leu Leu Cys Phe Thr Glu Arg Leu Glu Asp Leu Val Cys Phe Trp
        50                  55                  60 gag gaa gcg gcg agc gct ggg gtg ggc ccg ggc aac tac agc ttc tcc     240
Glu Glu Ala Ala Ser Ala Gly Val Gly Pro Gly Asn Tyr Ser Phe Ser
65                  70                  75                  80 tac cag ctc gag gat gag cca tgg aag ctg tgt cgc ctg cac cag gct     288
Tyr Gln Leu Glu Asp Glu Pro Trp Lys Leu Cys Arg Leu His Gln Ala
                85                  90                  95 ccc acg gct cgt ggt gcg gtg cgc ttc tgg tgt tcg ctg cct aca gcc     336
Pro Thr Ala Arg Gly Ala Val Arg Phe Trp Cys Ser Leu Pro Thr Ala
            100                 105                 110 gac acg tcg agc ttc gtg ccc cta gag ttg cgc gtc aca gca gcc tcc     384
Asp Thr Ser Ser Phe Val Pro Leu Glu Leu Arg Val Thr Ala Ala Ser
        115                 120                 125 ggc gct ccg cga tat cac cgt gtc atc cac atc aat gaa gta gtg ctc     432
Gly Ala Pro Arg Tyr His Arg Val Ile His Ile Asn Glu Val Val Leu
    130                 135                 140 cta gac gcc ccc gtg ggg ctg gtg gcg cgg ttg gct gac gag agc ggc     480
Leu Asp Ala Pro Val Gly Leu Val Ala Arg Leu Ala Asp Glu Ser Gly
145                 150                 155                 160 cac gta gtg ttg cgc tgg ctc ccg ccg cct gag aca ccc atg acg tct     528
His Val Val Leu Arg Trp Leu Pro Pro Pro Glu Thr Pro Met Thr Ser
                165                 170                 175 cac atc cgc tac gag gtg gac gtc tcg gcc ggc aac ggc gca ggg agc     576
His Ile Arg Tyr Glu Val Asp Val Ser Ala Gly Asn Gly Ala Gly Ser
            180                 185                 190 gta cag agg gtg gag atc ctg gag ggc cgc acc gag tgt gtg ctg agc     624
Val Gln Arg Val Glu Ile Leu Glu Gly Arg Thr Glu Cys Val Leu Ser
        195                 200                 205 aac ctg cgg ggc cgg acg cgc tac acc ttc gcc gtc cgc gcg cgt atg     672
Asn Leu Arg Gly Arg Thr Arg Tyr Thr Phe Ala Val Arg Ala Arg Met
    210                 215                 220 gct gag ccg agc ttc ggc ggc ttc tgg agc gcc tgg tcg gag cct gtg     720
Ala Glu Pro Ser Phe Gly Gly Phe Trp Ser Ala Trp Ser Glu Pro Val
225                 230                 235                 240 tcg ctg ctg acg cct agc gac ctg gac ccc ctc atc ctg acg ctc tcc     768
Ser Leu Leu Thr Pro Ser Asp Leu Asp Pro Leu Ile Leu Thr Leu Ser
                245                 250                 255 ctc atc ctc gtg gtc atc ctg gtg ctg ctg acc gtg ctc gcg ctg ctc     816
Leu Ile Leu Val Val Ile Leu Val Leu Leu Thr Val Leu Ala Leu Leu
            260                 265                 270
```

-continued

```
tcc cac cgc cgg gct ctg aag cag aag atc tgg cct ggc atc ccg agc       864
Ser His Arg Arg Ala Leu Lys Gln Lys Ile Trp Pro Gly Ile Pro Ser
        275                 280                 285 cca gag agc gag ttt gaa ggc ctc ttc acc acc cac aag ggt aac ttc       912
Pro Glu Ser Glu Phe Glu Gly Leu Phe Thr Thr His Lys Gly Asn Phe
    290                 295                 300 cag gta ggt ggc ctg gtt gtc ccc tca gtg cct ggg ctt ccc tgc ttc       960
Gln Val Gly Gly Leu Val Val Pro Ser Val Pro Gly Leu Pro Cys Phe
305                 310                 315                 320 ttg cag cca aac tgc agg cct ctc tga                                   987
Leu Gln Pro Asn Cys Arg Pro Leu
                325
```

<210> SEQ ID NO 9
<211> LENGTH: 328
<212> TYPE: PRT
<213> ORGANISM: Homo sapiens

<400> SEQUENCE: 9

```
Met Asp His Leu Gly Ala Ser Leu Trp Pro Gln Val Gly Ser Leu Cys
1               5                   10                  15

Leu Leu Leu Ala Gly Ala Ala Trp Ala Pro Pro Asn Leu Pro Asp
            20                  25                  30

Pro Lys Phe Glu Ser Lys Ala Ala Leu Leu Ala Ala Arg Gly Pro Glu
        35                  40                  45

Glu Leu Leu Cys Phe Thr Glu Arg Leu Glu Asp Leu Val Cys Phe Trp
    50                  55                  60

Glu Glu Ala Ala Ser Ala Gly Val Gly Pro Gly Asn Tyr Ser Phe Ser
65                  70                  75                  80

Tyr Gln Leu Glu Asp Glu Pro Trp Lys Leu Cys Arg Leu His Gln Ala
                85                  90                  95

Pro Thr Ala Arg Gly Ala Val Arg Phe Trp Cys Ser Leu Pro Thr Ala
            100                 105                 110

Asp Thr Ser Ser Phe Val Pro Leu Glu Leu Arg Val Thr Ala Ala Ser
        115                 120                 125

Gly Ala Pro Arg Tyr His Arg Val Ile His Ile Asn Glu Val Val Leu
    130                 135                 140

Leu Asp Ala Pro Val Gly Leu Val Ala Arg Leu Ala Asp Glu Ser Gly
145                 150                 155                 160

His Val Val Leu Arg Trp Leu Pro Pro Glu Thr Pro Met Thr Ser
                165                 170                 175

His Ile Arg Tyr Glu Val Asp Val Ser Ala Gly Asn Gly Ala Gly Ser
            180                 185                 190

Val Gln Arg Val Glu Ile Leu Glu Gly Arg Thr Glu Cys Val Leu Ser
        195                 200                 205

Asn Leu Arg Gly Arg Thr Arg Tyr Thr Phe Ala Val Arg Ala Arg Met
    210                 215                 220

Ala Glu Pro Ser Phe Gly Gly Phe Trp Ser Ala Trp Ser Glu Pro Val
225                 230                 235                 240

Ser Leu Leu Thr Pro Ser Asp Leu Asp Pro Leu Ile Leu Thr Leu Ser
                245                 250                 255

Leu Ile Leu Val Val Ile Leu Val Leu Leu Thr Val Leu Ala Leu Leu
            260                 265                 270

Ser His Arg Arg Ala Leu Lys Gln Lys Ile Trp Pro Gly Ile Pro Ser
        275                 280                 285
```

-continued

```
Pro Glu Ser Glu Phe Glu Gly Leu Phe Thr Thr His Lys Gly Asn Phe
    290                 295                 300

Gln Val Gly Gly Leu Val Val Pro Ser Val Pro Gly Leu Pro Cys Phe
305                 310                 315                 320

Leu Gln Pro Asn Cys Arg Pro Leu
                325

<210> SEQ ID NO 10
<211> LENGTH: 804
<212> TYPE: DNA
<213> ORGANISM: Homo sapiens
<220> FEATURE:
<221> NAME/KEY: CDS
<222> LOCATION: (1)..(801)
<223> OTHER INFORMATION: EpoR Isoform 4, intron 5 unspliced

<400> SEQUENCE: 10 atg gac cac ctc ggg gcg tcc ctc tgg ccc cag gtc ggc tcc ctt tgt     48
Met Asp His Leu Gly Ala Ser Leu Trp Pro Gln Val Gly Ser Leu Cys
1               5                   10                  15 ctc ctg ctc gct ggg gcc gcc tgg gcg ccc ccg cct aac ctc ccg gac     96
Leu Leu Leu Ala Gly Ala Ala Trp Ala Pro Pro Pro Asn Leu Pro Asp
                20                  25                  30 ccc aag ttc gag agc aaa gcg gcc ttg ctg gcg gcc cgg ggg ccc gaa    144
Pro Lys Phe Glu Ser Lys Ala Ala Leu Leu Ala Ala Arg Gly Pro Glu
            35                  40                  45 gag ctt ctg tgc ttc acc gag cgg ttg gag gac ttg gtg tgt ttc tgg    192
Glu Leu Leu Cys Phe Thr Glu Arg Leu Glu Asp Leu Val Cys Phe Trp
        50                  55                  60 gag gaa gcg gcg agc gct ggg gtg ggc ccg ggc aac tac agc ttc tcc    240
Glu Glu Ala Ala Ser Ala Gly Val Gly Pro Gly Asn Tyr Ser Phe Ser
65                  70                  75                  80 tac cag ctc gag gat gag cca tgg aag ctg tgt cgc ctg cac cag gct    288
Tyr Gln Leu Glu Asp Glu Pro Trp Lys Leu Cys Arg Leu His Gln Ala
                85                  90                  95 ccc acg gct cgt ggt gcg gtg cgc ttc tgg tgt tcg ctg cct aca gcc    336
Pro Thr Ala Arg Gly Ala Val Arg Phe Trp Cys Ser Leu Pro Thr Ala
            100                 105                 110 gac acg tcg agc ttc gtg ccc cta gag ttg cgc gtc aca gca gcc tcc    384
Asp Thr Ser Ser Phe Val Pro Leu Glu Leu Arg Val Thr Ala Ala Ser
        115                 120                 125 ggc gct ccg cga tat cac cgt gtc atc cac atc aat gaa gta gtg ctc    432
Gly Ala Pro Arg Tyr His Arg Val Ile His Ile Asn Glu Val Val Leu
    130                 135                 140 cta gac gcc ccc gtg ggg ctg gtg gcg cgg ttg gct gac gag agc ggc    480
Leu Asp Ala Pro Val Gly Leu Val Ala Arg Leu Ala Asp Glu Ser Gly
145                 150                 155                 160 cac gta gtg ttg cgc tgg ctc ccg ccg cct gag aca ccc atg acg tct    528
His Val Val Leu Arg Trp Leu Pro Pro Pro Glu Thr Pro Met Thr Ser
                165                 170                 175 cac atc cgc tac gag gtg gac gtc tcg gcc ggc aac ggc gca ggg agc    576
His Ile Arg Tyr Glu Val Asp Val Ser Ala Gly Asn Gly Ala Gly Ser
            180                 185                 190 gta cag agg gtg gag atc ctg gag ggc cgc acc gag tgt gtg ctg agc    624
Val Gln Arg Val Glu Ile Leu Glu Gly Arg Thr Glu Cys Val Leu Ser
        195                 200                 205 aac ctg cgg ggc cgg acg cgc tac acc ttc gcc gtc cgc gcg cgt atg    672
Asn Leu Arg Gly Arg Thr Arg Tyr Thr Phe Ala Val Arg Ala Arg Met
    210                 215                 220
```

-continued

```
gct gag ccg agc ttc ggc ggc ttc tgg agc gcc tgg tcg gag cct gtg    720
Ala Glu Pro Ser Phe Gly Gly Phe Trp Ser Ala Trp Ser Glu Pro Val
225                 230                 235                 240 tcg ctg ctg acg cct agc ggt gag gcc cca ggc ggg ggt gta gga gga    768
Ser Leu Leu Thr Pro Ser Gly Glu Ala Pro Gly Gly Gly Val Gly Gly
            245                 250                 255 gcc agg gcg aat cac ggg gca agc cca ccg ccc tga                    804
Ala Arg Ala Asn His Gly Ala Ser Pro Pro Pro
        260                 265
```

<210> SEQ ID NO 11
<211> LENGTH: 267
<212> TYPE: PRT
<213> ORGANISM: Homo sapiens

<400> SEQUENCE: 11

```
Met Asp His Leu Gly Ala Ser Leu Trp Pro Gln Val Gly Ser Leu Cys
1               5                   10                  15

Leu Leu Leu Ala Gly Ala Ala Trp Ala Pro Pro Asn Leu Pro Asp
                20                  25                  30

Pro Lys Phe Glu Ser Lys Ala Ala Leu Leu Ala Ala Arg Gly Pro Glu
            35                  40                  45

Glu Leu Leu Cys Phe Thr Glu Arg Leu Glu Asp Leu Val Cys Phe Trp
 50                  55                  60

Glu Glu Ala Ala Ser Ala Gly Val Gly Pro Gly Asn Tyr Ser Phe Ser
65                  70                  75                  80

Tyr Gln Leu Glu Asp Glu Pro Trp Lys Leu Cys Arg Leu His Gln Ala
                85                  90                  95

Pro Thr Ala Arg Gly Ala Val Arg Phe Trp Cys Ser Leu Pro Thr Ala
            100                 105                 110

Asp Thr Ser Ser Phe Val Pro Leu Glu Leu Arg Val Thr Ala Ala Ser
        115                 120                 125

Gly Ala Pro Arg Tyr His Arg Val Ile His Ile Asn Glu Val Val Leu
    130                 135                 140

Leu Asp Ala Pro Val Gly Leu Val Ala Arg Leu Ala Asp Glu Ser Gly
145                 150                 155                 160

His Val Val Leu Arg Trp Leu Pro Pro Pro Glu Thr Pro Met Thr Ser
                165                 170                 175

His Ile Arg Tyr Glu Val Asp Val Ser Ala Gly Asn Gly Ala Gly Ser
            180                 185                 190

Val Gln Arg Val Glu Ile Leu Glu Gly Arg Thr Glu Cys Val Leu Ser
        195                 200                 205

Asn Leu Arg Gly Arg Thr Arg Tyr Thr Phe Ala Val Arg Ala Arg Met
    210                 215                 220

Ala Glu Pro Ser Phe Gly Gly Phe Trp Ser Ala Trp Ser Glu Pro Val
225                 230                 235                 240

Ser Leu Leu Thr Pro Ser Gly Glu Ala Pro Gly Gly Gly Val Gly Gly
                245                 250                 255

Ala Arg Ala Asn His Gly Ala Ser Pro Pro Pro
            260                 265
```

<210> SEQ ID NO 12
<211> LENGTH: 747
<212> TYPE: DNA
<213> ORGANISM: Homo sapiens

```
<220> FEATURE:
<221> NAME/KEY: CDS
<222> LOCATION: (1)..(744)
<223> OTHER INFORMATION: EpoR Isoform 5, exon 6 skipped

<400> SEQUENCE: 12 atg gac cac ctc ggg gcg tcc ctc tgg ccc cag gtc ggc tcc ctt tgt    48
Met Asp His Leu Gly Ala Ser Leu Trp Pro Gln Val Gly Ser Leu Cys
 1               5                  10                  15 ctc ctg ctc gct ggg gcc gcc tgg gcg ccc ccg cct aac ctc ccg gac    96
Leu Leu Leu Ala Gly Ala Ala Trp Ala Pro Pro Pro Asn Leu Pro Asp
             20                  25                  30 ccc aag ttc gag agc aaa gcg gcc ttg ctg gcg gcc cgg ggg ccc gaa   144
Pro Lys Phe Glu Ser Lys Ala Ala Leu Leu Ala Ala Arg Gly Pro Glu
         35                  40                  45 gag ctt ctg tgc ttc acc gag cgg ttg gag gac ttg gtg tgt ttc tgg   192
Glu Leu Leu Cys Phe Thr Glu Arg Leu Glu Asp Leu Val Cys Phe Trp
 50                  55                  60 gag gaa gcg gcg agc gct ggg gtg ggc ccg ggc aac tac agc ttc tcc   240
Glu Glu Ala Ala Ser Ala Gly Val Gly Pro Gly Asn Tyr Ser Phe Ser
 65                  70                  75                  80 tac cag ctc gag gat gag cca tgg aag ctg tgt cgc ctg cac cag gct   288
Tyr Gln Leu Glu Asp Glu Pro Trp Lys Leu Cys Arg Leu His Gln Ala
             85                  90                  95 ccc acg gct cgt ggt gcg gtg cgc ttc tgg tgt tcg ctg cct aca gcc   336
Pro Thr Ala Arg Gly Ala Val Arg Phe Trp Cys Ser Leu Pro Thr Ala
        100                 105                 110 gac acg tcg agc ttc gtg ccc cta gag ttg cgc gtc aca gca gcc tcc   384
Asp Thr Ser Ser Phe Val Pro Leu Glu Leu Arg Val Thr Ala Ala Ser
        115                 120                 125 ggc gct ccg cga tat cac cgt gtc atc cac atc aat gaa gta gtg ctc   432
Gly Ala Pro Arg Tyr His Arg Val Ile His Ile Asn Glu Val Val Leu
130                 135                 140 cta gac gcc ccc gtg ggg ctg gtg gcg cgg ttg gct gac gag agc ggc   480
Leu Asp Ala Pro Val Gly Leu Val Ala Arg Leu Ala Asp Glu Ser Gly
145                 150                 155                 160 cac gta gtg ttg cgc tgg ctc ccg ccg cct gag aca ccc atg acg tct   528
His Val Val Leu Arg Trp Leu Pro Pro Pro Glu Thr Pro Met Thr Ser
                165                 170                 175 cac atc cgc tac gag gtg gac gtc tcg gcc ggc aac ggc gca ggg agc   576
His Ile Arg Tyr Glu Val Asp Val Ser Ala Gly Asn Gly Ala Gly Ser
            180                 185                 190 gta cag agg gtg gag atc ctg gag ggc cgc acc gag tgt gtg ctg agc   624
Val Gln Arg Val Glu Ile Leu Glu Gly Arg Thr Glu Cys Val Leu Ser
        195                 200                 205 aac ctg cgg ggc cgg acg cgc tac acc ttc gcc gtc cgc gcg cgt atg   672
Asn Leu Arg Gly Arg Thr Arg Tyr Thr Phe Ala Val Arg Ala Arg Met
210                 215                 220 gct gag ccg agc ttc ggc ggc ttc tgg agc gcc tgg tcg gag cct gtg   720
Ala Glu Pro Ser Phe Gly Gly Phe Trp Ser Ala Trp Ser Glu Pro Val
225                 230                 235                 240 tcg ctg ctg acg cct agc ggg ctc tga                               747
Ser Leu Leu Thr Pro Ser Gly Leu
                245

<210> SEQ ID NO 13
<211> LENGTH: 248
<212> TYPE: PRT
<213> ORGANISM: Homo sapiens
```

-continued

```
<400> SEQUENCE: 13

Met Asp His Leu Gly Ala Ser Leu Trp Pro Gln Val Gly Ser Leu Cys
1               5                   10                  15

Leu Leu Leu Ala Gly Ala Ala Trp Ala Pro Pro Asn Leu Pro Asp
            20                  25                  30

Pro Lys Phe Glu Ser Lys Ala Ala Leu Leu Ala Arg Gly Pro Glu
        35                  40                  45

Glu Leu Leu Cys Phe Thr Glu Arg Leu Glu Asp Leu Val Cys Phe Trp
    50                  55                  60

Glu Glu Ala Ala Ser Ala Gly Val Gly Pro Gly Asn Tyr Ser Phe Ser
65                  70                  75                  80

Tyr Gln Leu Glu Asp Glu Pro Trp Lys Leu Cys Arg Leu His Gln Ala
                85                  90                  95

Pro Thr Ala Arg Gly Ala Val Arg Phe Trp Cys Ser Leu Pro Thr Ala
            100                 105                 110

Asp Thr Ser Ser Phe Val Pro Leu Glu Leu Arg Val Thr Ala Ala Ser
        115                 120                 125

Gly Ala Pro Arg Tyr His Arg Val Ile His Ile Asn Glu Val Val Leu
    130                 135                 140

Leu Asp Ala Pro Val Gly Leu Val Ala Arg Leu Ala Asp Glu Ser Gly
145                 150                 155                 160

His Val Val Leu Arg Trp Leu Pro Pro Pro Glu Thr Pro Met Thr Ser
                165                 170                 175

His Ile Arg Tyr Glu Val Asp Val Ser Ala Gly Asn Gly Ala Gly Ser
            180                 185                 190

Val Gln Arg Val Glu Ile Leu Glu Gly Arg Thr Glu Cys Val Leu Ser
        195                 200                 205

Asn Leu Arg Gly Arg Thr Arg Tyr Thr Phe Ala Val Arg Ala Arg Met
    210                 215                 220

Ala Glu Pro Ser Phe Gly Gly Phe Trp Ser Ala Trp Ser Glu Pro Val
225                 230                 235                 240

Ser Leu Leu Thr Pro Ser Gly Leu
                245

<210> SEQ ID NO 14
<211> LENGTH: 22
<212> TYPE: DNA
<213> ORGANISM: Artificial sequence
<220> FEATURE:
<223> OTHER INFORMATION: Synthetic oligonucleotide

<400> SEQUENCE: 14
tcaagcggct gcttccttcc aa                                          22

<210> SEQ ID NO 15
<211> LENGTH: 24
<212> TYPE: DNA
<213> ORGANISM: Artificial sequence
<220> FEATURE:
<223> OTHER INFORMATION: Synthetic oligonucleotide

<400> SEQUENCE: 15
gcagggagcg tacagagggt ggag                                        24

<210> SEQ ID NO 16
<211> LENGTH: 24
<212> TYPE: DNA
<213> ORGANISM: Artificial sequence
```

-continued

```
<220> FEATURE:
<223> OTHER INFORMATION: Synthetic oligonucleotide

<400> SEQUENCE: 16
gaagaaatag caccaacctg gaag                                              24

<210> SEQ ID NO 17
<211> LENGTH: 22
<212> TYPE: DNA
<213> ORGANISM: Artificial sequence
<220> FEATURE:
<223> OTHER INFORMATION: Synthetic oligonucleotide

<400> SEQUENCE: 17
ctgacgccta gcgacctgga cc                                                22

<210> SEQ ID NO 18
<211> LENGTH: 21
<212> TYPE: DNA
<213> ORGANISM: Artificial sequence
<220> FEATURE:
<223> OTHER INFORMATION: Synthetic oligonucleotide

<400> SEQUENCE: 18
gcagtttggc tgcaagaagc a                                                 21

<210> SEQ ID NO 19
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 19
ggagccaggg cgaatcacgg                                                   20

<210> SEQ ID NO 20
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 20
gccttcaaac tcgctctctg                                                   20

<210> SEQ ID NO 21
<211> LENGTH: 21
<212> TYPE: DNA
<213> ORGANISM: Artificial sequence
<220> FEATURE:
<223> OTHER INFORMATION: Synthetic oligonucleotide

<400> SEQUENCE: 21
gcttcagagc ccgctaggcg t                                                 21
```

USE OF CYTOKINE RECEPTORS AS BIOMARKERS AND THERAPEUTIC TARGETS IN HUMAN CANCER

CLAIM FOR PRIORITY AND CROSS-REFERENCE TO OTHER APPLICATIONS

This application claims priority to and is a divisional of parent application Ser. No. 10/625,137 filed Jul. 23, 2003, now U.S. Pat. No. 7,160,697, which claims priority to provisional application Ser. No. 60/404,870 filed Aug. 21, 2002, the disclosures of which are hereby incorporated herein by reference in their entirety.

FIELD OF THE INVENTION

The present invention concerns nucleic acids encoding erythropoietin receptor isoforms, proteins encoded by such nucleic acids, antibodies that bind to such proteins, and methods of using the same.

BACKGROUND OF THE INVENTION

Erythropoietin (Epo) is the principal hematopoietic growth factor that promotes the viability, differentiation and proliferation of mammalian erythroid progenitor cells (S. Krantz, Blood 77, 419-34 (1991)). The biologic effects of Epo are mediated via its interaction with its specific transmembrane receptor, EpoR (H., Youssoufian, Blood 81, 2223-36 (1993)). The EpoR lacks intrinsic tyrosine kinase activity and upon ligand binding activates a receptor-associated tyrosine kinase Jak2 which is critical for anti-apoptosis and mitogenic signaling via the EpoR (O. Miura et al., Blood 84, 1501-7 (1994); B. Witthuhn et al., Cell 74, 227-36 (1993); J. Ihle, Nature 337, 591-4 (1995); H. Zhuang et al., J. Biol Chem. 270, 14500-4 (1995)). Activated Jak2 then phosphorylates a number of cytoplasmic proteins as well as the EpoR itself. Expression of Epo receptors has been reported on several non-hematopoietic cell types including vascular endothelial cells, placental tissue, neuronal cells, kidney and cardiomyocytes (A. Anagnostou et al., Proc. Natl. Acad. Sci. USA 91, 3974-8 (1994); S. Masuda et al., J. Biol. Chem. 268, 112-8-16 (1993); S. Sawyer et al., Blood 74, 103-9 (1989); M. Wald et al., J. Cell. Physiol. 167, 461-8 (1996)).

Recombinant human Epo (r-HuEpo) has been widely used in many different types of cancers for the treatment or prevention of chemo-radiotherapy induced anemia (A. Moliterno and J. Spivak, Hematol. Oncol. Clin. North Am. 10, 345-63 (1996)). For instance, in patients with breast cancer, r-HuEpo has been investigated in clinical trials for its potential beneficial effects in the prevention or treatment of chemotherapy or radiation therapy-related anemia (L. Del Mastro et al., J. Clin. Oncol. 15, 2715-21 (1997); H. Ludwig et al., Ann. Oncol. 4, 161-7 (1993); P. Sweeney et al., Br. J. Cancer 77, 1996-2002 (1998); S. Vijayakumar et al., Int. J. Radiat. Oncol. Biol. Phys 26, 721-9 (1993)), for mobilization of peripheral blood progenitor cells (C. Waller et al., Bone Marrow Transplant 24, 19-24 (1999)), to increase the rate of hematopoietic recovery following high dose chemotherapy (P. Benedetti Panici et al., Br. J. Cancer 75, 1205-12 (1997); S. Filip et al., Neoplasma 46, 166-72 (1999)) as well as use in ex vivo expansion strategies of stem cells (C. Bachier et al., Exp Hematol. 27, 615-23 (1999); L. Pierelli et al., Exp. Hematol. 27, 416-24 (1999); P. Stiff et al., Blood 95, 2169-74 (2000); W. Vogel et al., Blood 86, 1362-7 (1996)). Similarly, r-HuEpo has been investigated in several clinical trials of squamous cell cancers of head-neck (F. Dunphy et al., Cancer 86, 1362-7 (1999); M. Henke et al., radiother Oncol 50, 185-90 (1999); G. Mantovani et al., Oncol. Rep. 6, 421-6 (1999)) and uterine cervix (K. Dusenbery et al., Int. J. Radiat. Oncol. Biol. Phys. 29, 1079-84 (1994)).

In view of the foregoing, it would be extremely desirable to understand the association of Epo with tumor growth and how EpoR may be involved in cancer pathophysiology and progression.

SUMMARY OF THE INVENTION

A first aspect of the present invention is an isolated nucleic acid encoding erythropoietin receptor isoform 1, erythropoietin receptor isoform 2, erythropoietin receptor isoform 3, erythropoietin receptor isoform 4, or erythropoietin receptor isoform 5, or a nucleic acid thatencodes the opposite or complementary strand of a nucleic acid as set forth above (e.g., a DNA encoding an RNA).

A second aspect of the present invention is a protein encoded by a nucleic acid as described above (e.g., an isolated and/or purified protein).

A third aspect of the present invention is an antibody that selectively or specifically binds to a protein as described above.

A further aspect of the present invention is an oligonucleotide probe that selectively or specifically binds to a nucleic acid as described above.

A further aspect of the present invention is a method of screening a subject for cancer, comprising: detecting the presence or absence of a nucleic acid encoding an isoform as described above in the subject, the presence of such a nucleic acid indicating the subject is afflicted with or at risk of developing cancer.

A further aspect of the present invention is a method of screening a subject for cancer, comprising detecting the presence or absence of a protein or isoform as described above in the subject, the presence of such a protein indicating the subject is afflicted with or at risk of developing cancer.

Particular cancers which may be screened by the methods described herein include, but are not limited to, breast, cervix, ovarian, prostate, colon and lung cancer.

The foregoing and other objects and aspects of the present invention are explained in detail in the drawings herein and the specification set forth below.

BRIEF DESCRIPTION OF THE DRAWINGS

FIG. 2. Changes in the open reading frames (ORFs) of mature mRNA sequences from the full-length wild-type receptor in the isoforms of EpoR described herein. Isoform 1 (SEQ ID NO: 4): Additional nucleotides from intron 6 (nucleotides 5949-6062, SEQ ID NO: 1) are spliced between exons 6 and 7. Isoform 2 (SEQ ID NO: 6): Splicing at the 5' end of exon 8 occurs 19 nucleotides upstream (nucleotide 7498) from that seen in the full-length wild-type message (nucleotide 7517). Isoform 3 (SEQ ID NO: 8): Intron 7 is not spliced out of the final message. Isoform 4 (SEQ ID NO: 10): Intron 5 is not spliced out of the final message. Isoform 5 (SEQ ID NO: 12): exon 6 is skipped, with exon 5 spliced directly to exon 7. Putative C-terminal amino acid sequence changes from wild-type EpoR are depicted in bold.

DETAILED DESCRIPTION OF THE PREFERRED EMBODIMENTS

Figure 1:
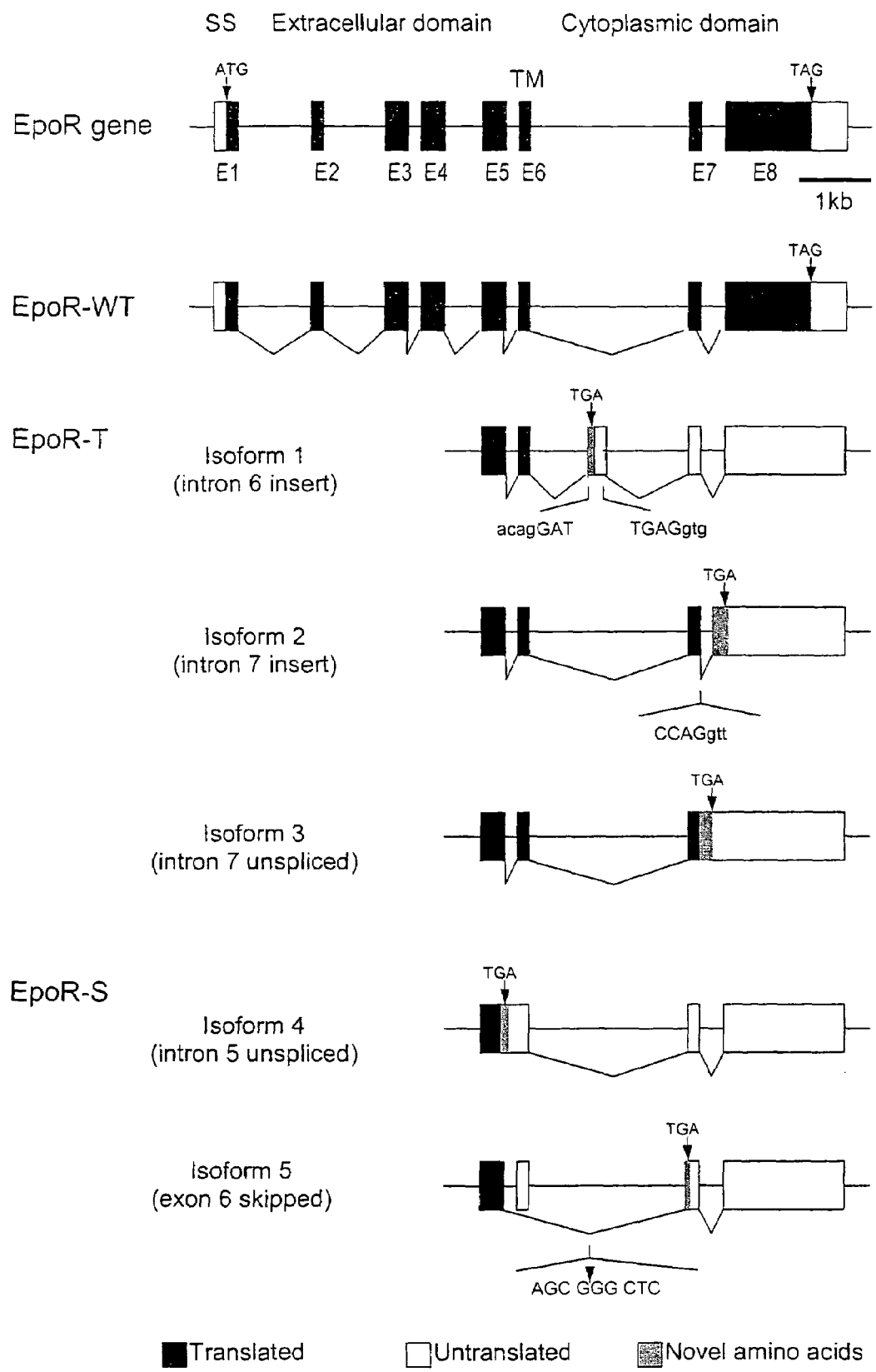
FIG. 1. The organization of the EpoR gene (GenBank accession number S45332, SEQ ID NO: 1). The splicing that results in the mature mRNA for the wild-type receptor (SEQ ID NO: 3), and five alternatively spliced isoforms (1-5) described herein are depicted schematically. The translated regions of the gene are indicated in black, whereas untranslated regions are indicated in white. Novel amino acid translations that result from alternative splicing of the EpoR gene transcript are indicated in grey.

The present invention is explained in greater detail below. This description is not intended to be a detailed catalog of all the different ways in which the invention may be implemented or all the features that may be added to the instant invention. For example, features illustrated with respect to one embodiment may be incorporated into other embodiments, and features illustrated with respect to a particular embodiment may be deleted from that embodiment. In addition, numerous variations and additions to the various embodiments suggested herein will be apparent to those skilled in the art in light of the instant disclosure which do not depart from the instant invention. Hence, the following specification is intended to illustrate some particular embodiments of the invention, and not to exhaustively specify all permutations, combinations and variations thereof.

Nucleic acid as used herein refers to any type of nucleic acid, including naturally occurring and synthetic nucleic acids and including both DNA and RNA.

Subjects with which the present invention may be carried out are generally mammalian subjects, including both human subjects and non-human subjects (e.g. dog, cat, horse, rabbit, rat) for veterinary or research purposes.

Any type of antibody may be used in the present invention. The term "antibodies" as used herein refers to all types of immunoglobulins, including TgG, IgM, IgA, IgD, and IgE. Of these, IgM and IgG are particularly preferred. The antibodies may be monoclonal or polyclonal (with monoclonal antibodies preferred) and may be of any species of origin, including (for example) mouse, rat, rabbit, horse, or human. See, e.g., M. Walker et al., *Molec. Immunol.* 26, 403-11 (1989). Antibody fragments that retain specific binding to the protein or epitope bound by the antibody are included within the scope of the term "antibody" and include, for example, Fab, F(ab')2, and Fc fragments, and the corresponding fragments obtained from antibodies other than IgG. Such fragments can be produced by known techniques. The antibodies may be chimeric or humanized, particularly when they are used for therapeutic purposes.

Applicants specifically intend that all United States patent references cited herein be incorporated herein by reference in their entirety.

1. Nucleic acids.

As noted above, a first aspect of the present invention is a nucleic acid encoding an erythropoieitin receptor isoform as described herein. In certain embodiments the nucleic acid may be an RNA such as an mRNA, or may be a DNA.

In one embodiment, the nucleic acid encodes erythropoietin receptor isoform 1 and has the sequence given herein as SEQ ID NO: 4.

In another embodiment, the nucleic acid encodes erythropoietin receptor isoform 2 and has the sequence given herein as SEQ ID NO: 6.

In another embodiment, the nucleic acid encodes erythropoietin receptor isoform 3 and has the sequence given herein as SEQ ID NO: 8.

In another embodiment, the nucleic acid encodes erythropoietin receptor isoform 4 and has the sequence given herein as SEQ ID NO: 10.

In another embodiment, the nucleic acid encodes erythropoietin receptor isoform 5 and has the sequence given herein as SEQ ID NO: 12.

In another embodiment, the nucleic acid that encodes the opposite strand of a nucleic acid as set forth above (e.g., is a DNA encoding an RNA).

Nucleic acids as described above may be natural or synthetic, and can be produced in accordance with techniques known in the art or variations thereof which will be apparent in light of the disclosure herein.

Nucleic acids as described above may be coupled to appropriate regulatory elements such as a promoter to produce a recombinant nucleic acid construct, which construct may be inserted into a host cell in which the promoter is operable so that the encoded protein is expressed by the host cell. Recombinant techniques and the production of proteins in recombinant cells may be carried out in accordance with known techniques.

2. Antibodies.

Polyclonal antibodies used to carry out the present invention may be produced by immunizing a suitable animal (e.g., rabbit, goat, etc.) with the antigen to which the monoclonal antibody binds, collecting immune serum from the animal, and separating the polyclonal antibodies from the immune serum, in accordance with known procedures. Depending on the host species, various adjuvants may be used to increase immunological response. Such adjuvants include, but are not limited to, Freund's, mineral gels such as aluminum hydroxide, and surface active substances such as lysolecithin, pluronic polyols, polyanions, peptides, oil emulsions, keyhole limpet hemocyanin, and dinitrophenol. Among adjuvants used in humans, BCG (bacilli Calmette-Guerin) and *Corynebacterium parvum* are especially preferable.

Monoclonal antibodies of the present invention may be prepared using any technique which provides for the production of antibody molecules by continuous cell lines in culture. These include, but are not limited to, the hybridoma technique, the human B-cell bybridoma technique, and the EBV-hybridoma technique (Kohler, G. et al. (1975) *Nature* 256: 495-497; Kozbor, D. et al. (1985) *J. Immunol. Methods* 81:31-42; Cote, R. J. et al. (1983) *Proc. Natl. Acad. Sci.* 80:2026-2030; Cole, S. P. et al. (1984) *Mol. Cell Biol.* 62:109-120). Briefly, the procedure is as follows: an animal is immunized with antigen or immunogenic fragments or conjugates thereof. For example, haptenic oligopeptides of antigen can be conjugated to a carrier protein to be used as an immunogen. Lymphoid cells (e.g. splenic lymphocytes) are then obtained from the immunized animal and fused with immortalizing cells (e.g. myeloma or heteromyeloma) to produce hybrid cells. The hybrid cells are screened to identify those which produce the desired antibody.

Human hybridomas which secrete human antibody can be produced by the Kohler and Milstein technique. Although human antibodies are especially preferred for treatment of human, in general, the generation of stable human-human hybridomas for long-term production of human monoclonal antibody can be difficult. Hybridoma production in rodents, especially mouse, is a very well established procedure and thus, stable murine hybridomas provide an unlimited source of antibody of select characteristics. As an alternative to human antibodies, the mouse antibodies can be converted to chimeric murine/human antibodies by genetic engineering techniques. See V. T. Oi et al., *Bio Techniques* 4(4):214-221 (1986); L. K. Sun et al., *Hybridoma* 5 (1986).

In addition, techniques developed for the production of "chimeric antibodies", the splicing of mouse antibody genes to human antibody genes to obtain a molecule with appropriate antigen specificity and biological activity can be used (S. L. Morrison, et al. *Proc. Natl. Acad. Sci.* 81, 6851-6855 (1984); M. S. Neuberger et al., *Nature* 312:604-608 (1984); S. Takeda, S. et al., *Nature* 314:452-454 (1985)). Alternatively, techniques described for the production of single chain antibodies may be adapted, using methods known in the art, to produce isoform-specific single chain antibodies. Antibodies with related specificity, but of distinct idiotypic composition, may be generated by chain shuffling from random combinatorial immunoglobin libraries (D. R. Burton, *Proc. Natl. Acad. Sci.* 88,11120-3 (1991)).

Antibodies may also be produced by inducing in vivo production in the lymphocyte population or by screening immunoglobulin libraries or panels of highly specific binding reagents as disclosed in the literature (R. Orlandi et al., *Proc. Natl. Acad. Sci.* 86, 3833-3837 (1989)); G. Winter et al., *Nature* 349, 293-299 (1991)).

Antibodies that selectively bind to a particular erythropoietin receptor isoform as described herein (i.e., that selectively bind to one of isoforms 1-5 but do not bind to the other of isoforms 1-5) can be identified in accordance with known techniques, such as their ability to compete with labeled antibody to in binding to that isoform in a competitive binding assay.

If desired, antibodies specific for a particular isoform can be used to produce anti-idiotypic (paratope-specific) antibodies. See e.g., McNamara et al., *Science* 220,1325-26 (1984), R. C. Kennedy, et al., *Science* 232,220 (1986).

3. Immunoassay Techniques.

Those skilled in the art will be familiar with numerous specific immunoassay formats and variations thereof which may be useful for carrying out the method disclosed herein. See generally E. Maggio, Enzyme-Immunoassay, (1980)(CRC Press, Inc., Boca Raton, Fla.); see also U.S. Pat. No. 4,727,022 to Skold et al. titled "Methods for Modulating Ligand-Receptor Interactions and their Application," U.S. Pat. No. 4,659,678 to Forrest et al. titled "Immunoassay of Antigens," U.S. Pat. No. 4,376,110 to David et al., titled "Immunometric Assays Using Monoclonal Antibodies," U.S. Pat. No. 4,275,149 to Litman et al., titled "Macromolecular Environment Control in Specific Receptor Assays," U.S. Pat. No. 4,233,402 to Maggio et al., titled "Reagents and Method Employing Channeling," and U.S. Pat. No. 4,230,767 to Boguslaski et al., titled "Heterogenous Specific Binding Assay Employing a Coenzyme as Label."

Antibodies as described herein may be coupled or conjugated to a solid support suitable for a diagnostic assay (e.g., beads, plates, slides or wells formed from materials such as latex or polystyrene) in accordance with known techniques, such as precipitation. Antibodies as described herein may likewise be coupled or conjugated to detectable groups such as radiolabels (e.g., $^{35}$S, $^{125}$I, $^{131}$I), enzyme labels (e.g., horseradish peroxidase, alkaline phosphatase), fluorescent labels (e.g., fluorescein), chemiluminescent labels (e.g., acridinium groups, metalloporphyrins such as phthalocyanine dyes, luminol, etc.), metal atoms (e.g., technetium-99m), etc., in accordance with known techniques. See, e.g., U.S. Pat. No. 4,472,509 to Gansow (metal chelates to monoclonal antibodies); U.S. Pat. No. 5,061,641 to Schochat et al.; and U.S. Pat. No. 4,861,869 to Nicoleotti et al. (radiolabelling proteins).

Immunoassays, or other types of assays to detect and/or quantitate the level of the isoform in samples as described below, may be used in screening assays to detect pathologic states associated with aberrant levels of isoform expression (e.g., tumors, inflammatory states), diagnostic studies, prognostic studies, or to monitor the progression or diminution of isoform expression in correlation with disease state.

Samples that may be collected for use in carrying out the immunoassay may be tissue samples from the organ or tissue of interest within the subject, such tissue generally of most interest being those types of tissues/cells that express differing amounts of isoform in pathologic states as compared to non-pathologic states, or biological fluids such as blood (including blood fractions such as blood plasma or blood serum), urine, cerebrospinal fluid, etc). Examples may include overexpression or aberrant expression of the isoform in various types of malignancies (e.g ovarian cancer, endometrial cancer, pancreatic cancer, breast cancer, urinary bladder cancer, lung cancer, etc.), as well as overexpression or aberrant expression in other pathologic states.

A biological sample may be a cell sample, with an intervening culturing step being performed between the time the cell sample is collected from the subject and the immunoassay is carried out on the biological sample.

For immunohistological techniques, a tissue sample is collected from the subject, and the presence or absence of binding of an antibody of the invention is detected. The presence of binding of the antibody in an abnormal pattern or a pattern indicative of a tumor or cancer indicates the presence of a tumor or cancer in the subject from which the tissue sample is collected. The presence of the antigen in a metastatic tumor deposit can also be used to determine a likely source of the primary tumor. Any suitable immunohistology format may be used. The tissue sample may include patient biopsies, resections or cells for cytologic study. A similar technique to immunohistology is the use of similar techniques to detect and/or phenotype cells in body fluids or other suspensions as is used for flow cytometric examination.

For in vivo diagnostic purposes the antibody according to the invention is coupled to or provided with a suitable externally detectable label, such as e.g. a radiolabel as described above or a metal atom (e.g., technetium-99m), and administered to a subject (e.g., by intraveneous or intraarterial injection), in an amount sufficient to produce an externally detectable signal, whereupon the possible localized accumulation of antibody in the body is determined, with a localized accumulation of the antibody (in a region other than that which would ordinarily be expected for normal subjects or subjects free of disease) indicating the present of a tumor in that subject.

4. Nucleic Acid Assay Techniques.

Detection of mRNAs specific to EpoR isoforms 1, 2, 3, 4, and 5 may be carried out by any suitable technique, including but not limited to using reverse transcriptase-polymerase chain reaction (RT-PCR) amplification with isoform-specific primers and Southern blot analysis of the resulting RT-PCR amplicons. For example, PolyA$^+$ RNA may be isolated by any technique known by those skilled in the art from patients patient cells and/or cancer cells, including but not limited to breast, colon, lung, ovary, and prostate cells or cancer cells. Methods for RT-PCR amplification of the isolated RNA are known in the art and may be carried out using EpoR isoform-specific primer pairs, preferably as described below.

Oligonucleotide probes (or primers) that specifically bind to a nucleic acid encoding an isoform as described above (including the opposite strands thereof), and pairs of probes (where at least one member of the pair is specific for a nucleic acid encoding one particular isoform), are also an aspect of the present invention. In general, such probes are from 8 or 10 nucleic acids in length up to 40 or 50 nucleic acids in length, or more. By "specifically bind" is meant that a probe binds to a nucleic acid (or complement thereof) that encodes one isoform as described herein, but does not bind to a nucleic acid (or complement thereof) that encodes another isoform as described herein. Probes may optionally be labeled with a detectable group such as a radioisotope, enzyme, or member of a binding pair in some assay formats.

Where a pair of probes or primers is used for amplification, it will be appreciated that only one member of the pair need be isoform-specific, and that the other member of the pair may be one which will bind to nucleic acids encoding more than one of the isoforms described herein, so long as the primer pair specifically amplifies only nucleic acid encoding one of the isoforms described herein. Examples of such oligonucleotide probes, and pairs thereof, are as follows:

```
Primer pair specific for intron 6 insert
(isoform 1)
                                  (SEQ ID NO: 14)
28AS-: 5' TCA AGC GGC TGC TTC CTT CCA A 3'

(SEQ ID NO: 15)
ER4-5: 5' GCA GGG AGC GTA CAG AGG GTG GAG 3'

Primer pair specific for intron 7 insert
(isoform 2)
                                  (SEQ ID NO: 16)
33AS:  5' GAA GAA ATA GCA CCA ACC TGG AAG 3'

(SEQ ID NO: 17)
31S:   5' CTG ACG CCT AGC GAC CTG GAC C 3'

Primer pair specific for intron 7 unspliced
(isoform 3)
                                  (SEQ ID NO: 18)
31AS:  5' GCA GTT TGG CTG CAA GAA GCA 3'

(SEQ ID NO: 17)
31S:   5' CTG ACG CCT AGC GAC CTG GAC C 3'

Primer pair specific for intron 5 unspliced
(isoform 4)
                                  (SEQ ID NO: 19)
26S:   5' GGA GCC AGG GCG AAT CAC GG 3'

(SEQ ID NO: 20)
32S:   5' GCC TTC AAA CTC GCT CTC TG 3'

Primer pair specific for exon 6 skipped
(isoform 5)
                                  (SEQ ID NO: 21)
34AS   5' GCT TCA GAG CCC GCT AGG CGT 3'

(SEQ ID NO: 15)
ER4-5  5' GCA GGG AGC GTA CAG AGG GTG GAG 3'
```

Note that, in the foregoing pairs, the primers of SEQ ID NO. 14, 16, 18, 19 and 21 are specific for the identified isoform, and the primers of SEQ ID NO. 15, 17 and 20 are not specific. In each pair, only one primer need be specific to provide an isoform-specific primer pair.

Blotting techniques are well known in the art. See, e.g., Sambrook et al., *Molecular Clooning: a Laboratory Manual* 3rd Ed. (Cold Spring Harbor, NY.); Ausubel et al. *Current Protocols in Molecular Biology* (Green Publishing Associates, Inc. and John Wiley & Sons, Inc., New York). The nucleic acids resulting from RT-PCR amplification may be separated by gel electrophoresis and immobilized on a suitable matrix, e.g. a filter of nitrocellulose. The presence of target sequences among the amplification products may be shown by incubation of the blotted amplicons with a probe (usually labeled) under conditions that promote denaturation and rehybridization. Because the probe is designed to base pair with target sequences, the probe will bind under renaturing conditions. Unbound probe is then removed, and detection of target sequences may be accomplished via known techniques to detect the labeled probe.

The present invention and the various methods and compounds therein are explained in greater detail in the following non-limiting examples.

EXAMPLE 1

The Erythropoietin Receptor (EpoR) gene. The human EpoR gene has been cloned and sequenced as previously described (Noguchi et al. (1991) *Blood* 78:2548-2556). The gene spans 8.6 kilobases, and comprises of 8 exons with 7 intervening introns, the latter of which range in size from 81 bp to 2.1 kb. The organization of the EpoR gene is outlined in FIG. 1. The full-length wild-type form of EpoR comprises of 508 amino acids (SEQ ID NO: 2) in three domains: extracellular, transmembrane (TM), and cytoplasmic. Exons 1-5 encode for the extracellular domain of EpoR, exon VI encodes for the transmembrane domain, while exons VII and VIII encode for the cytoplasmic domain of the receptor. In the examination of EpoR expression in tumor vasculature, analysis by RT-PCR indicated a high level of EpoR mRNA expression in breast cancer cells, as well as squamous cell cancers of head-neck and uterine cervix was observed.

EXAMPLE 2

Novel Isoforms of EpoR mRNA Transcripts. The resulting RT-PCR amplification products derived from human cervix, breast, prostate, and ovarian cancer cell lines were sequenced and analyzed. The results of this study revealed five alternatively spliced EpoR mRNA transcripts that differ from the mature, full-length wild-type EpoR mRNA. Using isoform-specific PCR primers, transcripts corresponding to each isoform were detected in breast, colon, lung, ovarian and prostate cancer. The organization of these five isoforms is outlined in FIG. 1. The alternative forms of EpoR predicted to be coded for from these alternatively spliced mRNAs fall into two categories isoforms 1, 2, and 3 are described as truncated (EpoR-T), and possess the extracellular and transmembrane domains of the wild-type receptor, while lacking portions of the cytoplasmic domain. Isoforms 4 and 5 are described as soluble (EpoR-S), and only possess the extracellular domain of the wild-type receptor intact. The changes in the putative C-terminal amino acid sequence encoded by these mRNAs are outlined in FIG. 2.

EXAMPLE 3

EpoR Isoform 1. The mRNA that codes for Isoform 1 contains an additional 114 nucleotides from intron 6 (nucleotides 5949-6062, SEQ ID NO: 1) spliced between exons 6 and 7. The resulting mRNA will code for an EpoR peptide 285 amino acids in length (SEQ ID NO: 5) with a severe truncation in the cytoplasmic region. At the C-terminal, 9 novel amino acids (M V R E G S R R R STOP) inserted at position 277 of the full-length EpoR peptide sequence.

EXAMPLE 4

EpoR Isoform 2. The mRNA that codes for Isoform 2 is the result of an alternative splicing event between the 3' end of exon 7 and 5' end of exon 8, in which an additional 19 nucleotides (nucleotides 7498-7516, SEQ ID NO: 1) are added to the 5' end of exon 8. The mRNA from this splicing event codes for an EpoR peptide 317 amino acids in length (SEQ ID NO: 7) with a severe truncation in the cytoplasmic domain, in which 12 novel amino acids (V G A I S S A V A V P E STOP) are inserted at position 306 of the EpoR peptide sequence. As with Isoform 1, Isoform 2 also possesses a truncation of the cytoplasmic domain of the full-length peptide sequence of EpoR.

EXAMPLE 5

EpoR Isoform 3. The translation of isoform 3 results from a processed EpoR mRNA in which sequences from intron 7 (nucleotides 7422-7516, SEQ ID NO: 1) are not spliced out of the final message. The resulting translation is a 328 amino acid peptide (SEQ ID NO: 9), with 23 novel amino acids introduced to the C-terminus (V G G L V V P S V P G L P C F L Q P N C R P L STOP) at position 306 of the EpoR peptide sequence. As with Isoforms 1 and 2, Isoform 3 possesses a truncation of the cytoplasmic domain of the full-length peptide sequence of EpoR. The sequence of the ORF of the mRNA message (SEQ ID NO: 8) and the peptide sequence of EpoR Isoform 3 (SEQ ID NO: 9) is identical to the translation predicted from an mRNA described previously (Nakamura et al. (1992) Science 257:1138-1141).

EXAMPLE 6

EpoR Isoform 4. The processed EpoR mRNA that translates into Isoform 4 contains sequences from intron 5 (nucleotides 5061-5144, SEQ ID NO: 1) are not spliced out of the final message. The resulting translation is a 267 amino acid peptide (SEQ ID NO: 11) with 21 novel amino acids (G E A P G G G V G G A R A N H G A S P P P STOP) introduced to the C-terminus at position 247 of the full-length EpoR peptide sequence. This isoform of EpoR possesses neither the transmembrane nor cytoplasmic domains of the full-length receptor. The translation that codes for Isoform 4 results in a soluble form of EpoR, containing the extracellular domain of the receptor only.

EXAMPLE 7

EpoR Isoform 5. Isoform 6 is a translation that results from the alternatively processed EpoR mRNA in which sequences from exon 6 are skipped, i.e. exons 5 and 7 are spliced together directly. The translation of this message results in a 248 amino acid peptide (SEQ ID NO: 13), in which 2 novel amino acids (G L STOP) are introduced at position 247 of the full-length peptide sequence of EpoR. As with Isoform 4, Isoform 5 of EpoR is a soluble form of the receptor that comprises of only the extracellular domain.

The foregoing is illustrative of the present invention, and is not to be construed as limiting thereof. The invention is defined by the following claims, with equivalents of the claims to be included therein.

That which is claimed is:

1. An isolated nucleic acid selected from the group consisting of
   a nucleic acid encoding erythropoietin receptor isoform 2 and having the sequence given herein as SEQ ID NO: 6; and
   a nucleic acid that is the full length complement of SEQ ID NO:6.

2. The nucleic acid according to claim 1 encoding erythropoietin receptor isoform 2 and having the sequence given herein as SEQ ID NO: 6.

3. The nucleic acid according to claim 1, wherein said nucleic acid is an RNA.

4. A recombinant nucleic acid comprising a promoter operatively associated with a nucleic acid according to claim 1.

5. An isolated host cell in culture containing a recombinant nucleic acid according to claim 4 and which expresses the encoded erythropoetin receptor isoform.

6. A method of screening a subject for cancer, comprising: detecting the presence or absence of a nucleic acid according to claim 1 in said subject, the presence of such a nucleic acid indicating said subject is afflicted with cancer;
    wherein said cancer is selected from the group consisting of breast, lung, and ovarian cancer.

7. The method according to claim 6, wherein said cancer is breast cancer.

8. The method according to claim 6, wherein said detecting step is carried out by collecting a biological sample from said subject, and then detecting the presence or absence of said nucleic acid in said biological sample.

\* \* \* \* \*

UNITED STATES PATENT AND TRADEMARK OFFICE
CERTIFICATE OF CORRECTION

PATENT NO. : 7,598,057 B2
APPLICATION NO. : 11/512501
DATED : October 6, 2009
INVENTOR(S) : Arcasoy et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 357 days.

Signed and Sealed this

Twenty-eighth Day of September, 2010

David J. Kappos
*Director of the United States Patent and Trademark Office*